US008383088B2

(12) United States Patent
Wagner et al.

(10) Patent No.: US 8,383,088 B2
(45) Date of Patent: Feb. 26, 2013

(54) COUMESTAN-LIKE ANTIOXIDANTS AND UV ABSORBANTS

(75) Inventors: Barbara Wagner, Lörrach (DE); Sébastien Mongiat, Sierentz (FR); Bernd Herzog, Grenzach-Wyhlen (DE); Werner Baschong, Basel (CH); Andreas Buthe, Steinfurt (DE); Reinhold Öhrlein, Rheinfelden-Herten (DE)

(73) Assignee: BASF SE, Ludwigshafen (DE)

( * ) Notice: Subject to any disclaimer, the term of this patent is extended or adjusted under 35 U.S.C. 154(b) by 167 days.

(21) Appl. No.: 12/528,357

(22) PCT Filed: Feb. 29, 2008

(86) PCT No.: PCT/EP2008/052463
§ 371 (c)(1),
(2), (4) Date: Sep. 17, 2010

(87) PCT Pub. No.: WO2008/110465
PCT Pub. Date: Sep. 18, 2008

(65) Prior Publication Data
US 2010/0330009 A1    Dec. 30, 2010

(30) Foreign Application Priority Data
Mar. 9, 2007   (EP) .................................. 07103820

(51) Int. Cl.
*A61K 8/00* (2006.01)
*A61K 8/18* (2006.01)
*A61Q 17/04* (2006.01)
*A61Q 1/02* (2006.01)
*A61Q 19/04* (2006.01)
*A61Q 1/00* (2006.01)
*A61Q 1/12* (2006.01)
*A61Q 5/00* (2006.01)
*A61Q 9/00* (2006.01)

(52) U.S. Cl. .............. 424/59; 424/63; 424/69; 424/70.1
(58) Field of Classification Search .................. 424/59, 424/63, 69, 70.1
See application file for complete search history.

(56) References Cited

U.S. PATENT DOCUMENTS

| 5,714,134 A * | 2/1998 | Richard et al. .................. 424/59 |
| 6,852,326 B2 * | 2/2005 | Breton .......................... 424/401 |
| 2004/0126340 A1 | 7/2004 | Jo |

FOREIGN PATENT DOCUMENTS

| EP | 0 779 287 A1 | 6/1997 |
| WO | 02/092041 A1 | 11/2002 |

OTHER PUBLICATIONS

Leutbecher et al. Synlett 2005, 20, 3126-3130 (in IDS submitted Nov. 9, 2009).*
Leutbecher et al. (2005) Synlett, 20, 3126-3130.
Nematollahi & Forooghi (2002) Tetrahedron, 58, 4949-4953.
Fakhari et al., Electrochimica Acta 50 (2005) 5322-5328.
Pandey et al., Tetrahedron 45, 6867 (1989).
Krishnaswamy et al., Indian J. Chem. vol. 4, Mar. 1966.
Rani et al., JICS 64, 38 (1987).
Darbarwar et al., Ind. J. Chem. 11, 115 1973.
Darbarwar et al., Current Science, 38, 13 (Jan. 1969).

* cited by examiner

*Primary Examiner* — Fereydoun G Sajjadi
*Assistant Examiner* — Genevieve S Alley
(74) *Attorney, Agent, or Firm* — Shiela A. Loggins

(57) ABSTRACT

The present invention relates to derivatives of the 1H-pyrano [4,3-b]benzofuran-1-one structure and their nitrogen analogues which possess powerful antioxidant properties combined with a highly effective UV absorbing functionality in one molecule. These compounds are especially useful in cosmetical and dermatological formulations.

14 Claims, No Drawings

COUMESTAN-LIKE ANTIOXIDANTS AND UV ABSORBANTS

The present invention relates to derivatives of the 1H-pyrano[4,3-b]benzofuran-1-one structure and some nitrogen analogues which possess powerful antioxidant properties combined with a highly effective UV absorbing functionality in one molecule.

Phenolic compounds are the most intensively studied and widely used natural and synthetic antioxidants. Examples for various types of natural phenolic antioxidants are alpha-tocopherol, quercetin, morin, 3,4-dihydroxybenzoic acid, thymol and carvacrol among others. The vitamin alpha-tocopherol is the major lipid-soluble, chain-breaking antioxidant in human blood plasma and in low-density lipoprotein associates. Its mechanism of action as an antioxidant, and that of phenolic compounds in general, is believed to be the transfer of its phenolic H-atom to a chain-carrying peroxyl radical at a rate much faster than that at which the chain-propagating step of lipid peroxidation proceeds.

Many phenolic compounds used as antioxidants in food, cosmetics, personal care and household products are not always photochemically stable, which limits their utility. It is also well known that ultraviolet (UV) light is another important source of radical generation as well as of a number of biological adverse effects. Therefore UV absorbers in particular UV-B and UV-A absorbing compounds are applied to prevent free radical initiated damage to biological and chemical molecules during exposure to UV light.

Leutbecher et al. (2005) Synlett, 20, 3126-3130 describes Laccase-catalyzed domino reactions of 4-hydroxy-6-methyl-2H-pyran-2-one or substituted 4-hydroxy-2H-chromen-2-ones with catechols using molecular oxygen as an oxidant which afford coumestans and related O-heterocycles. Further, Nematollahi & Forooghi (2002) Tetrahedron, 58, 4949-4953 describe the electrochemical oxidation of catechols in the presence of 4-hydroxy-6-methyl-2-pyrone as nucleophile. The quinones derived from the catechols participate in Michael addition reactions with 4-hydroxy-6-methyl-2-pyrone. However, these references are completely silent with respect to both the antioxidant and UV absorbing properties of these compounds.

It has now been found that specific coumestan modifications, namely derivatives of the 1H-pyrano[4,3-b]benzofuran-1-one structure and their nitrogen analogues, surprisingly exhibit a number of interesting biological activities like antibacterial and antifungal effects, and possess, for example, powerful antioxidant properties combined with a highly effective UV absorbing functionality in one molecule.

The instant invention thus pertains to compositions containing compounds of general formula (I)

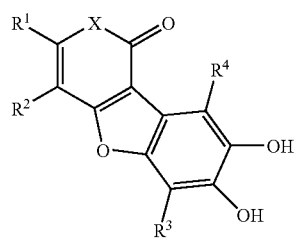

(I)

wherein
X is O, NH or $NR^{15}$, $R^1$, $R^2$ $R^3$ and $R^4$ are independently of each other H, halogen, especially fluorine, hydroxy, $C_1$-$C_{24}$alkyl, $C_1$-$C_{24}$alkyl which is substituted by at least one E and/or interrupted by at least one D, $C_1$-$C_{24}$ perfluoroalkyl, $C_6$-$C_{14}$perfluoroaryl, especially pentafluorophenyl, $C_5$-$C_{12}$cycloalkyl, $C_5$-$C_{12}$cycloalkyl which is substituted by G and/or interrupted by S—, —O—, or —$NR^{15}$—, —$NR^{15}R^{16}$, $C_1$-$C_{24}$alkylthio, —$PR^{17}R^{18}$, $C_5$-$C_{12}$cycloalkoxy, $C_5$-$C_{12}$cycloalkoxy which is substituted by G, $C_6$-$C_{24}$aryl, $C_6$-$C_{24}$aryl which is substituted by G, $C_1$-$C_{24}$alkyl, $C_5$-$C_{12}$cycloalkyl, $C_7$-$C_{25}$aralkyl, $C_1$-$C_{24}$ perfluoroalkyl, $C_6$-$C_{14}$perfluoroaryl, especially pentafluorophenyl, or $C_1$-$C_{24}$haloalkyl; $C_2$-$C_{20}$heteroaryl, $C_2$-$C_{20}$heteroaryl which is substituted by G, fluorine, $C_1$-$C_{24}$alkyl, $C_5$-$C_{12}$cycloalkyl, $C_7$-$C_{25}$aralkyl, $C_1$-$C_{24}$ perfluoroalkyl, $C_6$-$C_{14}$perfluoroaryl, especially pentafluorophenyl, or $C_1$-$C_{24}$haloalkyl; $C_2$-$C_{24}$alkenyl, $C_2$-$C_{24}$alkynyl, $C_1$-$C_{24}$alkoxy, $C_1$-$C_{24}$alkoxy which is substituted by at least one E and/or interrupted by at least one D, $C_7$-$C_{25}$aralkyl, $C_7$-$C_{25}$aralkyl, which is substituted by G, $C_7$-$C_{25}$aralkoxy, $C_7$-$C_{25}$aralkoxy which is substituted by G, or —CO—$R^{19}$, or $R^1$ and $R^2$ are a group

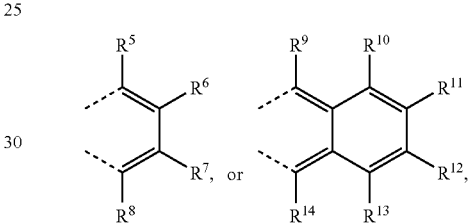

wherein $R^5$, $R^6$, $R^7$, $R^8$, $R^9$, $R^{10}$, $R^{11}$, $R^{12}$, $R^{13}$ and $R^{14}$ are independently of each other H, halogen, hydroxy, $C_1$-$C_{24}$alkyl, $C_1$-$C_{24}$alkyl which is substituted by at least one E and/or interrupted by at least one D, $C_1$-$C_{24}$ perfluoroalkyl, $C_6$-$C_{14}$perfluoroaryl, especially pentafluorophenyl, $C_5$-$C_{12}$cycloalkyl, $C_5$-$C_{12}$cycloalkyl which is substituted by at least one G and/or interrupted by at least one S—, —O—, or —$NR^{15}$—, $C_5$-$C_{12}$cycloalkoxy, $C_5$-$C_{12}$cycloalkoxy which is substituted by G, $C_6$-$C_{24}$aryl, $C_6$-$C_{24}$aryl which is substituted by at least one G, $C_2$-$C_{20}$heteroaryl, $C_2$-$C_{20}$heteroaryl which is substituted by at least one G, $C_2$-$C_{24}$alkenyl, $C_2$-$C_{24}$alkynyl, $C_1$-$C_{24}$alkoxy, $C_1$-$C_{24}$alkoxy which is substituted by at least one E and/or interrupted by at least one D, $C_7$-$C_{25}$aralkyl, $C_7$-$C_{25}$aralkyl, which is substituted by at least one G, $C_7$-$C_{25}$aralkoxy, $C_7$-$C_{25}$aralkoxy which is substituted by at least one G, or at least —CO—$R^{19}$, D is —CO—; —COO—; —S—; —SO—; —$SO_2$—; —O—; —$NR^{15}$—; —$POR^{17}$—; —$CR^{20}$=$CR^{21}$—; or —C≡C—;

E is —$OR^{22}$; —$SR^{22}$; —$NR^{15}R^{16}$; —[$NR^{15}R^{16}R^{24}$]$^+Z^-$; —$COR^{19}$; —$COOR^{23}$; —$CONR^{15}R^{16}$; —CN; —$N_3$; —$OCOOR^{23}$; or halogen; and G is E, or $C_1$-$C_{24}$alkyl, wherein $R^{20}$, $R^{21}$, $R^{15}$, $R^{16}$ and $R^{24}$ are independently of each other H; $C_6$-$C_{18}$aryl; $C_6$-$C_{18}$aryl which is substituted by $C_1$-$C_{24}$alkyl, or $C_1$-$C_{24}$alkoxy; $C_1$-$C_{24}$alkyl; or $C_1$-$C_{24}$alkyl which is interrupted by at least one —O—; or $R^{15}$ and $R^{16}$ together form a five or six membered ring, in particular

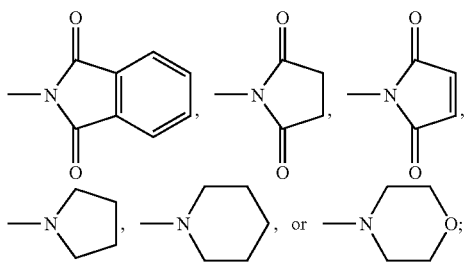

Z is halogen, preferably Cl;

$R^{19}$ and $R^{23}$ are independently of each other H; $C_6$-$C_{18}$aryl; $C_6$-$C_{18}$aryl which is substituted by $C_1$-$C_{24}$alkyl, or $C_1$-$C_{24}$alkoxy; $C_1$-$C_{24}$alkyl; or $C_1$-$C_{24}$alkyl which is interrupted by at least one —O—;

$R^{22}$ is H; $C_6$-$C_{18}$aryl; $C_6$-$C_{18}$aryl, which is substituted by $C_1$-$C_{24}$alkyl, or $C_1$-$C_{24}$alkoxy; $C_1$-$C_{24}$alkyl; or $C_1$-$C_{24}$alkyl which is interrupted by at least one —O—; and $R^{17}$ and $R^{18}$ are independently of each other $C_1$-$C_{24}$alkyl, $C_6$-$C_{18}$aryl, or $C_6$-$C_{18}$aryl, which is substituted by $C_1$-$C_{24}$alkyl;

$R^3$ and $R^4$ may further be a mono-, di- or oligosaccharide residue alpha- or beta-linked to the phenolic ring system either directly or via the phenolic oxygen.

A number of compounds of this class, especially those containing a saccharide and/or ammonium moiety, exhibit further interesting biological activities such as antibacterial and antifungal effects.

$R^3$ and/or $R^4$ as a mono-, di- or oligosaccharide residue alpha- or beta-linked to the phenolic ring system usually consists of hexose or pentose subunits or acylated hexose or pentose subunits. A hexose or pentose subunit often is selected from the group consisting of glucose, ribose, galactose, mannose, acylated (especially acetylated) derivatives thereof, or N-acetyl glucosamine, N-acetyl galactosamine, lactose, N-acetyl lactosamine.

Some compounds especially useful in the composition according to the invention are those, where in the compound of formula (I)

X is O, NH or $NR^{15}$, $R^1$ is $C_1$-$C_{24}$alkyl, $C_2$-$C_{24}$alkenyl, $C_1$-$C_{24}$alkoxy, or said alkyl, alkenyl or alkoxy which is substituted by E;

$R^2$ is H;

$R^3$ is H; hydroxy; $C_1$-$C_{24}$alkyl; $C_1$-$C_{24}$alkyl which is substituted by at least one E and/or interrupted by at least one D; $C_5$-$C_{12}$cycloalkyl; $C_5$-$C_{12}$cycloalkyl which is substituted by G and/or interrupted by —O— or —$NR^{15}$—; —$NR^{15}R^{16}$; $C_5$-$C_{12}$cycloalkoxy; $C_5$-$C_{12}$cycloalkoxy which is substituted by G; phenyl which is unsubstituted or substituted by G; $C_2$-$C_{24}$alkenyl; $C_1$-$C_{24}$alkoxy; $C_1$-$C_{24}$alkoxy which is substituted by at least one E and/or interrupted by at least one D; $C_7$-$C_{25}$phenylalkyl; $C_7$-$C_{25}$phenylalkyl, which is substituted by G; $C_7$-$C_{25}$phenylalkoxy; $C_7$-$C_{25}$phenylalkoxy which is substituted by G; or —OCO—$R^{19}$ or —CO—$R^{19}$;

$R^4$ is H; hydroxy; $C_1$-$C_{24}$alkyl which is unsubstituted or substituted by at least one E, and/or is interrupted by at least one D; $C_5$-$C_{12}$cycloalkoxy; $C_5$-$C_{12}$cycloalkoxy which is substituted by G; $C_1$-$C_{24}$alkoxy; $C_1$-$C_{24}$alkoxy which is substituted by at least one E and/or interrupted by at least one D; or —OCO—$R^{19}$ or —CO—$R^{19}$;

$R^3$ and/or $R^4$ may further be a mono-, di- or oligosaccharide residue alpha- or beta-linked to the phenolic ring system wherein said residue consists of hexose or pentose subunits and wherein at least one hexose or pentose subunit is selected from the group consisting of glucose, ribose, galactose, mannose, N-acetyl glucosamine, N-acetyl galactosamine, lactose and N-acetyl lactosamine;

D is —CO—, —COO—, or —O—;

G and E are independently of each other —$OR^{22}$; $NR^{15}R^{16}$; —$[NR^{15}R^{16}R^{24}]^+Z^-$; —$COR^{19}$; —$COOR^{23}$; —CN; —$N_3$; —$OCOOR^{23}$; or halogen; or G is $C_1$-$C_{12}$alkyl;

$R^{15}$ and $R^{16}$ and $R^{24}$ are independently of each other H; phenyl; phenyl which is substituted by $C_1$-$C_{24}$alkyl; or $C_1$-$C_{24}$alkoxy; $C_1$-$C_{24}$alkyl; or $C_1$-$C_{24}$alkyl which is interrupted by —O—;

$R^{19}$ is H; phenyl; phenyl which is substituted by $C_1$-$C_{24}$alkyl, hydroxy and/or $C_1$-$C_{24}$alkoxy; $C_{24}$alkyl; or $C_1$-$C_{24}$alkyl which is interrupted by —O—; phenoxy; phenoxy which is substituted by $C_1$-$C_{24}$alkyl, hydroxy and/or $C_1$-$C_{24}$alkoxy; $C_1$-$C_{24}$alkoxy; or $C_1$-$C_{24}$alkoxy which is interrupted by —O—;

$R^{22}$ and $R^{23}$ are independently of each other H; phenyl; phenyl which is substituted by $C_1$-$C_{24}$alkyl; $C_1$-$C_{24}$alkyl; or $C_1$-$C_{24}$alkyl which is interrupted by —O—;

and especially, where in the compound of formula (I)

X is O, NH or $NR^{15}$, $R^1$ is $C_1$-$C_{24}$alkyl, $C_2$-$C_{24}$alkenyl, or said alkyl or alkenyl substituted by —$NR^{15}R^{16}$ or —$N_3$ or —$[NR^{15}R^{16}R^{24}]^+Z^-$;

$R^2$ is H;

$R^3$ and $R^4$ independently are H; hydroxy; $C_1$-$C_{12}$alkyl; $C_2$-$C_{12}$alkenyl; $C_1$-$C_{12}$alkoxy; or —OCO—$R^{19}$ or —CO—$R^{19}$; or are a mono- or di-saccharide residue alpha- or beta-linked to the phenolic ring system wherein said residue consists of hexose or pentose subunits selected from the group consisting of glucose, ribose, galactose, mannose, N-acetyl glucosamine, N-acetyl galactosamine, lactose and N-acetyl lactosamine;

$R^{15}$, $R^{16}$ and $R^{24}$ are independently of each other H or $C_1$-$C_5$alkyl, and $Z^-$ is halogenide, especially chloride.

Some of the present compounds of the formula (I) are novel; these compounds represent a further embodiment of the invention. Novel compounds of the invention are those of the above formula (I) with exception of the following compounds:

7,8-dihydroxy-3,6-dimethyl-1H-pyrano[4,3-b]benzofuran-1-one;

7,8-dihydroxy-6-methoxy-3-methyl-1H-pyrano[4,3-b]benzofuran-1-one;

7,8-dihydroxy-3-methyl-1H-pyrano[4,3-b]benzofuran-1-one;

7,8-dihydroxy-3-methyl-1-oxo-1H-pyrano[4,3-b]benzofuran-9-carboxylic acid methyl ester;

9-fluoro-7,8-dihydroxy-3-methyl-1H-pyrano[4,3-b]benzofuran-1-one; and 6-fluoro-7,8-dihydroxy-3-methyl-1H-pyrano[4,3-b]benzofuran-1-one;

a compound of formula (I) wherein X is NH, $R^1$ is methyl, and $R^2$-$R^4$ each are hydrogen; and a compound of the formula (I) wherein $R^1$ and $R^2$ are a group

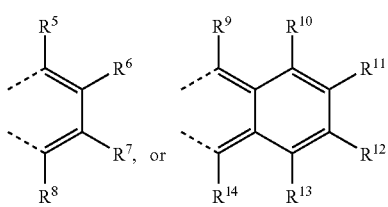

and each of $R^3$ and $R^4$ are selected from H, methyl, methoxy.

Novel compounds of specific technical interest include those of the formula (I), wherein $R^2$ is H, and at least one of the other residues contains an extended carbon chain, such as compounds wherein the sum of carbon atoms in $R^1$, $R^3$ and $R^4$ together is at least 4, especially 5 or more. Further preferred compounds of the invention are as described elsewhere for the compositions of the invention, with exception of the compounds excluded (see above).

Atom numberings are as shown in formula (I'):

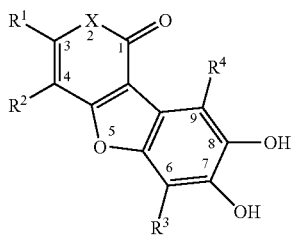

(I')

A further preferred embodiment of the invention concerns compounds of formula (I) wherein X is O and $R^3$ and/or $R^4$ is a mono-, di- or oligosaccharide residue alpha- or beta-linked to the phenolic ring system as indicated above wherein said residue consists of hexose or pentose subunits and wherein at least one hexose or pentose subunit is selected from the group consisting of glucose, ribose, galactose, mannose, N-acetyl glucosamine, N-acetyl galactosamine, lactose and N-acetyl lactosamine.

Yet another preferred embodiment of the invention is a compound of formula (I) wherein X is O;

$R^1$ is $C_1$-$C_{24}$alkyl, $C_2$-$C_{24}$alkenyl, or $C_1$-$C_{24}$alkyl which is substituted by —$OR^{22}$, —$COR^{19}$, —$COOR^{23}$, or —$OCOOR^{23}$E;

$R^2$ is H;

$R^3$ is H, $C_1$-$C_{24}$alkyl, $C_1$-$C_{24}$alkyl which is substituted by at least one E and/or interrupted by at least one D, $C_5$-$C_{12}$cycloalkyl, $C_5$-$C_{12}$cycloalkyl which is substituted by G and/or interrupted by S—, —O—, or —$NR^{15}$—, —$NR^{15}R^{16}$, $C_5$-$C_{12}$cycloalkoxy, $C_5$-$C_{12}$cycloalkoxy which is substituted by G, $C_6$-$C_{24}$aryl, $C_6$-$C_{24}$aryl which is substituted by G, $C_1$-$C_{24}$alkyl, $C_5$-$C_{12}$cycloalkyl, $C_7$-$C_{25}$aralkyl, $C_2$-$C_{24}$alkenyl, $C_1$-$C_{24}$alkoxy, $C_1$-$C_{24}$alkoxy which is substituted by at least one E and/or interrupted by at least one D, $C_7$-$C_{25}$aralkyl, $C_7$-$C_{25}$aralkyl, which is substituted by G, $C_7$-$C_{25}$aralkoxy, $C_7$-$C_{25}$aralkoxy which is substituted by G, or —CO—$R^{19}$, $R^4$ is hydroxyl, $C_1$-$C_{24}$alkyl which is substituted by at least one E and/or interrupted by at least one D, $C_5$-$C_{12}$cycloalkoxy, $C_5$-$C_{12}$cycloalkoxy which is substituted by G, $C_1$-$C_{24}$alkoxy, $C_1$-$C_{24}$alkoxy which is substituted by at least one E and/or interrupted by at least one D, or —CO—$R^{19}$, D is —CO—, —COO—, or —O—;

G and E are independently of each other —$OR^{22}$, —$COR^{19}$, —$COOR^{23}$, or —$OCOOR^{23}$;

wherein $R^{15}$ and $R^{16}$ are independently of each other H; $C_6$-$C_{18}$aryl; $C_6$-$C_{18}$aryl which is substituted by $C_1$-$C_{24}$alkyl, or $C_1$-$C_{24}$alkoxy; $C_1$-$C_{24}$alkyl; or $C_1$-$C_{24}$alkyl which is interrupted by —O—; or $R^{15}$ and $R^{16}$ together form a five or six membered ring, in particular

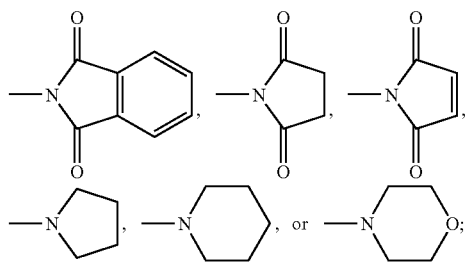

$R^{19}$ and $R^{23}$ are independently of each other H; $C_6$-$C_{18}$aryl; $C_6$-$C_{18}$aryl which is substituted by $C_1$-$C_{24}$alkyl, or $C_1$-$C_{24}$alkoxy; $C_1$-$C_{24}$alkyl; or $C_1$-$C_{24}$alkyl which is interrupted by —O—;

$R^{22}$ is H; $C_6$-$C_{18}$aryl; $C_6$-$C_{18}$aryl, which is substituted by $C_1$-$C_{24}$alkyl, or $C_1$-$C_{24}$alkoxy; $C_1$-$C_{24}$alkyl; or $C_1$-$C_{24}$alkyl which is interrupted by —O—; and $R^3$ and/or $R^4$ may further be a mono-, di- or oligosaccharide residue alpha- or beta-linked to the phenolic ring system as is indicated above wherein said residue consists of hexose or pentose subunits and wherein at least one hexose or pentose subunit is selected from the group consisting of glucose, ribose, galactose, mannose, N-acetyl glucosamine, N-acetyl galactosamine, lactose and N-acetyl lactosamine.

Still another preferred embodiment of the instant invention relates to compounds of general formula (I) wherein X is NH or $NR^{15}$, $R^1$ is H or $C_1$-$C_5$alkyl;

$R^2$, $R^3$ and $R^4$ are H; and wherein $R^{15}$ is $C_1$-$C_5$alkyl.

Examples of novel coumestane-like compounds according to the instant invention include, but are not limited to, compounds No. A-3 to A-6, A-9 to A-27, and B-1 to B-4 as identified below.

In another embodiment the instant invention also relates to a process for preparing the compounds of general formula (I) described hereinbefore, wherein said process comprises the step of reacting a compound of general formula (I-a) with a compound of general formula (I-b):

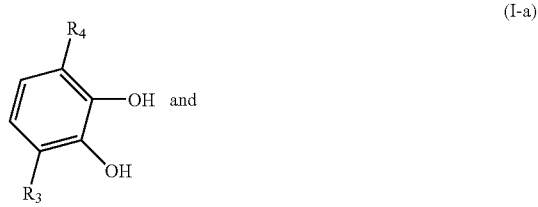

(I-a)

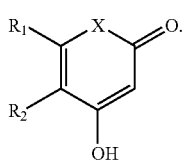

(I-b)

Preferably said reacting step is a catalyzed by a catecholase; examples are laccase-catalyzed or tyrosinase-catalyzed transformations of (I-a) with (I-b).

For example, the compounds according to the invention can be prepared according to a chemical method disclosed by D. Habibi et al. in Heterocyclic Communications, Vol. 11, No 2, in 2005 on the pages 145-148. The synthesis route comprises the oxidative coupling of in-situ generated o-benzoquinones with 4-hydroxy-6-methyl-2-pyrone.

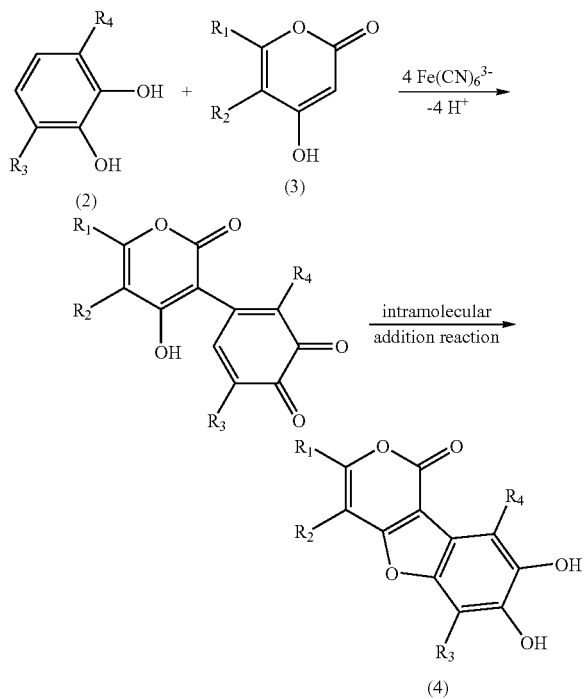

In a one pot method a catechol of formula (2) with $R_3$ and $R_4$ as defined above can be coupled with a 4-hydroxy-2-pyrone of formula (3) with $R_1$ and $R_2$ as defined above in the presence of potassium ferricyanide as the oxidizing agent leading to the corresponding 1H-pyrano[4,3-b]benzofuran-1-ones derivatives of formula (4).

Typically inorganic oxidants such as $K_3[Fe(CN)_6]$ are used, however also electrochemical (Nematollahi D., Forooghi Z. (2002) oxidation of catechols in the presence of 4-hydroxy-6-methyl-2-pyrone is possible. Tetrahedron Vol. 58, 4949-4953) describes an enzymatic (with e.g. tyrosinase or laccase) route.

U. Beifuss (Synlett 2005, No. 20, pages 3126-3130) for example describes the laccase-catalyzed transformation of catechols and 4-hydroxy-6-methyl-2-pyrone to 1H-pyrano[4,3-b]benzofuran-1-ones derivatives in the presence of oxygen. He uses commercially available laccase of *Trametes versicolor* as the enzyme.

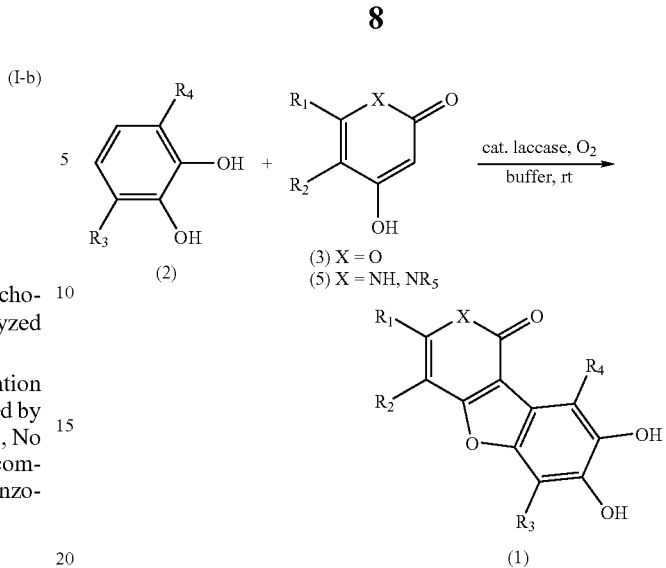

This method is applicable to a variety of different catechol structures of formula (2) and different 4-hydroxy-2-pyrone structures of formula (3) leading to the corresponding phenols of formula (4).

The enzymatic transformation is preferably carried out in an aqueous buffer system or a mixture with organic solvents or in sole organic solvents. The reaction temperature is between −20° C. and 100° C., more preferably between 0° C. and 40° C. and most preferably between 10° C. and 30° C. The enzymatic reaction is also suitable for the transformation of 4-hydroxy-2(1H)-pyridinones of formula (5) (with $R_1$ and $R_2$ as defined above) with suitable substituted catechols leading to the corresponding benzofuro(3,2-c)pyridin-1(2H)-one compounds. The 5,6-disubstituted 4-hydroxy-2-pyrone compounds can be synthesized by techniques known to a person skilled in the art.

The $R_1$ substituted 4-hydroxy-2-pyrones of formula (3) (with $R_2$=H) can be prepared by a procedure described by Katritzky et al. (2005, Org. Chem. Vol. 70, 4854-4856). The method is based on the reaction of 2,2,6-trimethyl-1,3-dioxin-4-one (6) with 1-acylbenzotriazols of formula (7) in the presence of LDA at low temperature. The resulting 2,2-dimethyl-6-(2-oxoalkyl)-1,3-dioxin-4-ones of formula (8) are converted via a thermal extrusion cyclization reaction into the $R_1$ substituted 4-hydroxy-2-pyrones of formula (3) with $R_2$ denoting hydrogen.

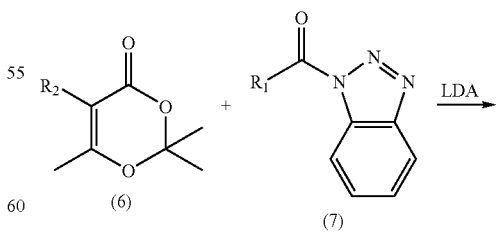

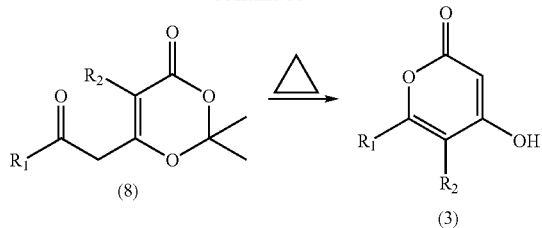

The $R_1$ and $R_2$ substituted 4-hydroxy-2(1H)-pyridinones of formula (5) can be prepared by a procedure described by Butt (J. Chem. Soc., 1963, page 4483). The method comprises the reaction of pyrandiones of formula (9) with amines of formula (10) to yield the corresponding pyridinones of formula (5):

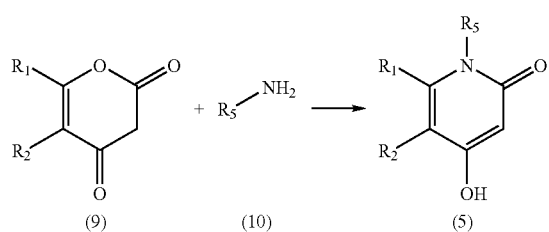

Another method of preparing pyridinones of formula (5) is described by D. B. Rubinov (Russian Journal of Organic Chemistry, Vol. 40, No. 9, 2004 on pages 1329-1331). 5-Acetoacetyl-2,2-dimethyl-1,3-dioxane-4,6-diones of formula (11) can be reacted with amines of formula (10) under mild conditions to give enamino compounds of formula (12). By heating of the latter compounds first in boiling toluene and then in diethylene glycol dimethyl ether the desired N-substituted pyridinones of formula (5) are obtained:

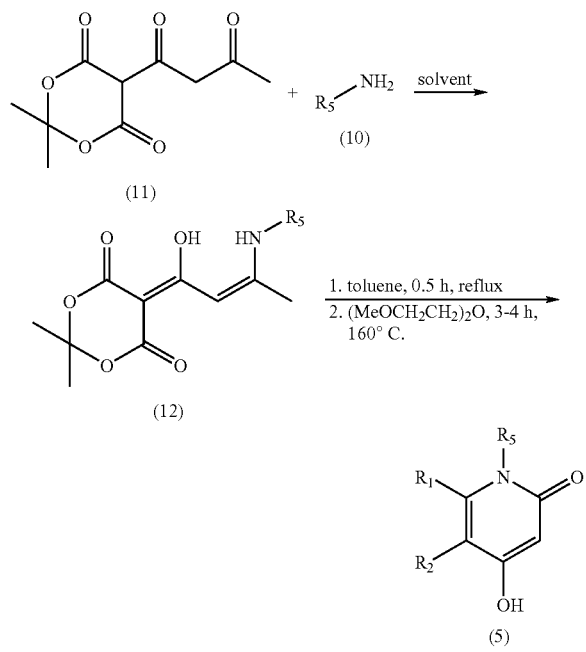

Halogen is fluorine, chlorine, bromine and iodine.

$C_1$-$C_{24}$alkyl is a branched or unbranched radical such as for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, icosyl or docosyl.

$C_1$-$C_{24}$ perfluoroalkyl is a branched or unbranched radical such as for example —$CF_3$, —$CF_2CF_3$, —$CF_2CF_2CF_3$, —$CF(CF_3)_2$, —$(CF_2)_3CF_3$, and —$C(CF_3)_3$.

$C_1$-$C_{24}$alkoxy radicals are straight-chain or branched alkoxy radicals, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy.

$C_2$-$C_{24}$alkenyl radicals are straight-chain or branched alkenyl radicals, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_{2-24}$alkynyl is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

$C_4$-$C_{18}$cycloalkyl, especially $C_5$-$C_{12}$cycloalkyl, is preferably $C_5$-$C_{12}$cycloalkyl or said cycloalkyl substituted by one to three $C_1$-$C_4$alkyl groups, such as, for example, cyclopentyl, methyl-cyclopentyl, dimethylcyclopentyl, cyclohexyl, methylcyclohexyl, dimethylcyclohexyl, trimethyl-cyclohexyl, tert-butylcyclohexyl, cycloheptyl, cyclooctyl, cyclononyl, cyclodecyl, cyclododecyl, 1-adamantyl, or 2-adamantyl. Cyclohexyl, 1-adamantyl and cyclopentyl are most preferred.

Examples of $C_4$-$C_{18}$cycloalkyl, which is interrupted by S, O, or $NR^{15}$, are piperidyl, piperazinyl and morpholinyl.

Aryl is usually $C_6$-$C_{30}$aryl, preferably $C_6$-$C_{24}$aryl, which optionally can be substituted, such as, for example, phenyl, 4-methylphenyl, 4-methoxyphenyl, naphthyl, biphenylyl, 2-fluorenyl, phenanthryl, anthryl, tetracyl, pentacyl, hexacyl, terphenylyl or quadphenylyl; or phenyl substituted by one to three $C_1$-$C_4$alkyl groups, for example o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

$C_7$-$C_{24}$aralkyl radicals are preferably $C_7$-$C_{15}$aralkyl radicals, which may be substituted, such as, for example, benzyl, 2-benzyl-2-propyl, β-phenethyl, α-methylbenzyl, α,α-dimethylbenzyl, ω-phenyl-butyl, ω-phenyl-octyl, ω-phenyl-dodecyl; or phenyl-$C_1$-$C_4$alkyl substituted on the phenyl ring by one to three $C_1$-$C_4$alkyl groups, such as, for example, 2-methylbenzyl, 3-methylbenzyl, 4-methylbenzyl, 2,4-dimethylbenzyl, 2,6-dimethylbenzyl or 4-tert-butylbenzyl or 3-methyl-5-(1',1',3',3'-tetramethyl-butyl)-benzyl.

Heteroaryl is typically $C_2$-$C_{26}$heteroaryl, i.e. a ring with five to seven ring atoms or a condensed ring system, wherein nitrogen, oxygen or sulfur are the possible hetero atoms, and is typically an unsaturated heterocyclic radical with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl, which can be unsubstituted or substituted.

$C_6$-$C_{18}$cycloalkoxy is, for example, cyclopentyloxy, cyclohexyloxy, cycloheptyloxy or cyclooctyloxy, or said cycloalkoxy substituted by one to three $C_1$-$C_4$alkyl, for example, methylcyclopentyloxy, dimethylcyclopentyloxy, methylcyclohexyloxy, dimethylcyclohexyloxy, trimethylcyclohexyloxy, or tert-butylcyclohexyloxy.

$C_6$-$C_{24}$aryloxy is typically phenoxy or phenoxy substituted by one to three $C_1$-$C_4$alkyl groups, such as, for example o-, m- or p-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2-methyl-6-ethylphenoxy, 4-tert-butylphenoxy, 2-ethylphenoxy or 2,6-diethylphenoxy.

$C_6$-$C_{24}$aralkoxy is typically phenyl-$C_1$-$C_9$alkoxy, such as, for example, benzyloxy, α-methylbenzyloxy, α,α-dimethylbenzyloxy or 2-phenylethoxy.

$C_1$-$C_{24}$alkylthio radicals are straight-chain or branched alkylthio radicals, such as e.g. methylthio, ethylthio, propylthio, isopropylthio, n-butylthio, isobutylthio, pentylthio, isopentyl-thio, hexylthio, heptylthio, octylthio, decylthio, tetradecylthio, hexadecylthio or octadecylthio.

Examples of a five or six membered ring are heterocycloalkanes or heterocycloalkenes having from 3 to 5 carbon atoms which can have one additional hetero atom selected from nitrogen, oxygen and sulfur, for example

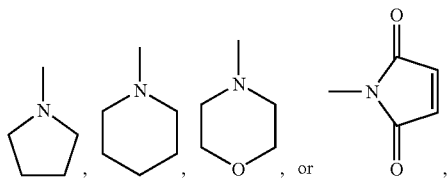

which can be part of a bicyclic system, for example

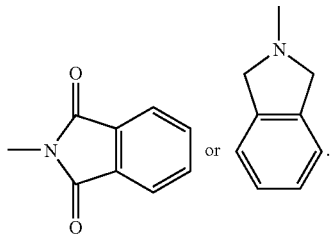

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group or a silyl group.

Acyl denotes a residue of an organic acid, especially of a carboxylic acid; examples are $C_1$-$C_{18}$alkanoyl or benzoyl, especially preferred is acetyl.

The term "haloalkyl" means groups given by partially or wholly substituting the above-mentioned alkyl group with halogen, such as trifluoromethyl etc. The "aldehyde group, ketone group, ester group, carbamoyl group and amino group" include those substituted by a $C_1$-$C_{24}$alkyl group, a $C_4$-$C_{18}$cycloalkyl group, an $C_6$-$C_{30}$aryl group, an $C_7$-$C_{24}$aralkyl group or a heterocyclic group, wherein the alkyl group, the cycloalkyl group, the aryl group, the aralkyl group and the heterocyclic group may be unsubstituted or substituted.

If a substituent occurs more than one time in a group, it can be different in each occurrence.

As described above, the aforementioned radicals may be substituted by at least one E and/or, if desired, interrupted by at least one D. Interruptions are of course possible only in the case of radicals containing at least 2 carbon atoms connected to one another by single bonds; $C_6$-$C_{18}$aryl is not interrupted; interrupted arylalkyl or alkylaryl contains the unit D in the alkyl moiety. $C_1$-$C_{24}$alkyl substituted by one or more E and/or interrupted by one or more units D is, for example, $(CH_2CH_2O)_{1-9}$—$R^x$, where $R^x$ is H or $C_1$-$C_{10}$alkyl or $C_2$-$C_{10}$alkanoyl (e.g. CO—CH($C_2H_5$)$C_4H_9$), $CH_2$—CH($OR^{y'}$)—$CH_2$—O—$R^y$, where $R^y$ is $C_1$-$C_{24}$alkyl, $C_5$-$C_{12}$cycloalkyl, phenyl, $C_7$-$C_{15}$-phenylalkyl, and $R^{y'}$ embraces the same definitions as $R^y$ or is H; $C_1$-$C_8$alkylene-COO—$R^z$, e.g. $CH_2COOR^z$, $CH(CH_3)COOR^z$, $C(CH_3)_2CO$-$OR^z$, where $R^z$ is H, $C_1$-$C_{24}$alkyl, $(CH_2CH_2O)_{1-9}$—$R^x$, and $R^x$ embraces the definitions indicated above; $CH_2CH_2$—O—CO—CH=$CH_2$; $CH_2CH(OH)CH_2$—O—CO—$C(CH_3)$=$CH_2$.

Especially preferred are compositions of the invention wherein the organic material is a synthetic polymer, preferably selected from the group consisting of polystyrenes, graft copolymers of styrene, polyphenylene oxides, polyphenylene sulfides, polyurethanes, polyisocyanates, aromatic polyesters, aromatic polyamides, polyureas, polyimides, polyamide-imides, polysulfones, polyethersulfones, polyetherketones, alkyd resins, aminoplast resins and epoxy resins.

Particularly preferred are compositions wherein the compound of component (b) is selected from the group consisting of:

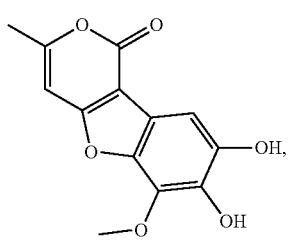 (A-1)
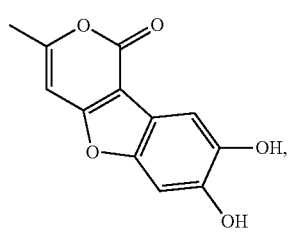 (A-2)
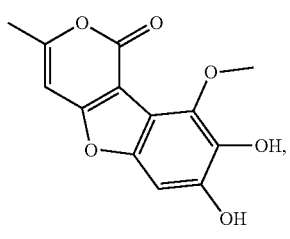 (A-3)
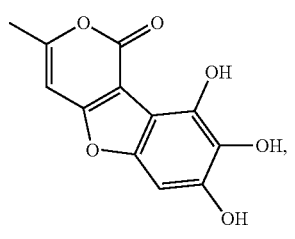 (A-4)
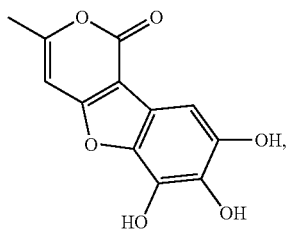 (A-5)
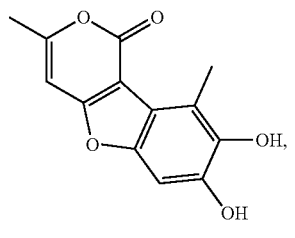 (A-6)
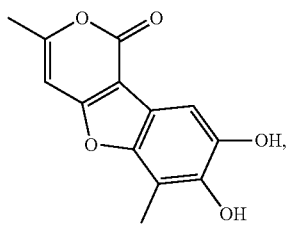 (A-7)
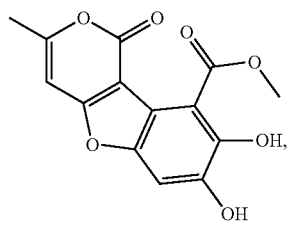 (A-8)
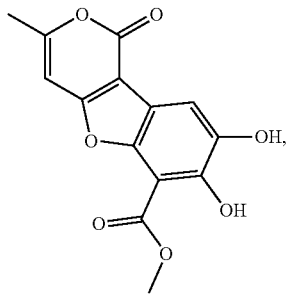 (A-9)
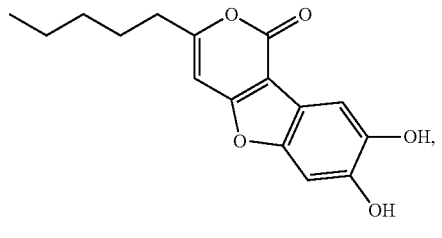 (A-10)
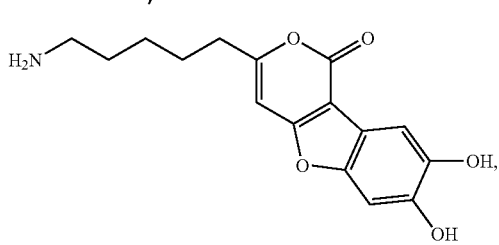 (A-11)
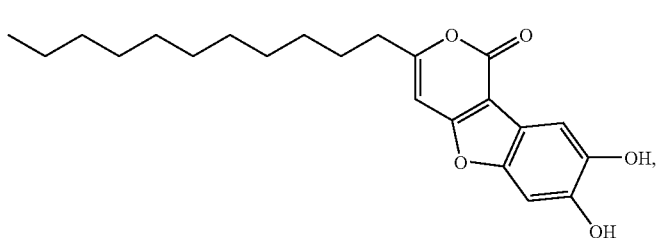 (A-12)
(A-13)

Additionally, the composition according to instant invention may further contain a UV absorber selected from the group consisting of the benzophenones, benzotriazoles, cyanoacrylic acid derivatives, hydroxyaryl-s-triazines, anthranilates, dibenzoyl methanes, benzylidene-dioxoimidazolines, benzylidene malonates, oxides like titanium dioxide and zinc ocide, salicylates, cinnamate derivatives, para-aminobenzoic acid derivatives, camphor derivatives, phenylbenzimidazoles, diphenylacrylates, organic nickel compounds and oxanilides, preferably said UV absorber is selected from the group consisting of 2-[2-hydroxy-3,5-di-(alpha,alpha-dimethylbenzyl)phenyl]-2H-benzotriazole, 2-(2-hydroxy-3, 5-di-tert-amylphenyl)-2H-benzotriazole, 2-[2-hydroxy-3-tert-butyl-5-(omega-hydroxy-octa(ethyleneoxy)carbonyl) ethylphenyl]-2H-benzotriazole, 2-[2-hydroxy-3-tert-butyl-5-(2-octyloxycarbonylethyl)phenyl]-2H-benzotriazole, 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2' ethyloxanilide, 2,6-bis(2,4-dimethylphenyl)-4-(2-hydroxy-4-octyloxyphenyl-s-triazine, 2,6-bis(2,4-dimethylphenyl)-4-(2,4-dihydroxyphenyl)-s-triazine, 2,4-bis(2,4-dihydroxyphenyl)-6-(4-chlorophenyl)-s-triazine, 2,6-bis(2,4-dimethylphenyl)-4-[2-hydroxy-4-(2-hydroxy-3-dodecyloxypropanoxy)phenyl]-s-triazine, and 2,2'-dihydroxy-4,4'-dimethoxybenzophenone. Of specific technical interest, especially for cosmetic formulations, is 2,4-bis-[(4-(2-ethylhexyloxy)-2-hydroxyphenyl)]-6-(4-methoxyphenyl)-1,3,5-triazine).

Particularly useful are also organic sunscreen agents like avobenzone, 2-ethylhexyl p-methoxycinnamate, 4,4'-t-butyl-methoxydibenzoylmethane, 2-hydroxy-4-methoxy benzophenone, octyldimethyl p-aminobenzoic acid, 2,2-dihydroxy-4-methoxybenzophenone, 2[4-(diethylamino)-2-hydroxybenzoyl]-benzoic acid hexyl ester, ethyl-4-[bis (hydroxyl propyl)]aminobenzoate, 2-ethylhexyl-2-cyano-3, 3-diphenylacrylate, di-(2-ethylhexyl)-3,5-dimethoxy-4-hydroxy benzylidene malonate, 2-ethylhexylsalicylate, glycerol p-amino benzoate, 3,3,5-trimethylcyclohexylsalicylate, methylanthranilate, menthyl anthranilate, p-dimethylaminobenzoic acid, 2-ethylhexyl p-dimethylaminobenzoate, 2-phenylbenzimidazole-5-sulfonic acid, 2-(p-dimethylamino phenyl-5-sulfoniobenzoxazoic acid, 2,2'-methylenebis[6-(2H-benzotriazol-2-yl)-4-(1,1,3,3-tetramethylbutyl)-phenol, 2-(4-methyl benzylidene)-camphor, 4-isopropyldibenzoyle methane, 2-(2H-benzotriazol-2-yl)-4-methyl-6-[2-methyl-3-[1,3,3,3-tetramethyl-1-[(trimethylsilyl)oxy]disiloxanyl]propyl]-phenol (CAS No. 155633-54-8), anisotriazone (CAS No. 191419-26-8), ethylhexyltriazone (Uvinul T 150), diethylhexylbutamidotriazone (CAS No. 154702-15-5) and mixtures thereof.

The compositions according to the present invention may contain additional antioxidants. Examples of suitable antioxidants include but are not limited to p-hydroxybenzoic acid and its derivatives (ethylisobutyl, glyceryl esters of p-hydroxybenzoic acid), salicylates (octylamyl, phenyl, benzyl menthyl, glycerol and dipropyleneglycol esters), coumarin derivatives, flavones, benzylidene malonates, phenylmethyl propanoic acid derivatives like [(4-hydroxy-3,5-dimethoxyphenyl)methyl]-propanedioic acid, bis(2-ethylhexyl) ester (CAS No. 872182-46-2), hydroxyl or methoxy substituted benzophenones, uric or tannic acid and its derivatives, hydroquinone, and benzophenones.

Further components additionally useful in the present compositions are listed further below, and in the publications referred to.

In general, polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1., for example mixtures of polypropylene with polyisobutylene.

3. Copolymers of monoolefins and diolefins with each other or with other vinyl monomers, such as, for example, ethylene/propylene, propylene/butene-1, propylenedisobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(alpha-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer, and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from alpha,beta-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrilebutadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.
13. Polyphenylene oxides and sulfides, and mixtures of polyphenylene oxides with polystyrene.
14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).
15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.
16. Polyureas, polyimides and polyamide-imides.
17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane]terephthalate and polyhydroxybenzoates as well as block-copolyether-esters derived from polyethers having hydroxyl end groups.
18. Polycarbonates.
19. Polysulfones, polyethersulfones and polyetherketones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low flammability.
23. Thermosetting acrylic resins, derived from substituted acrylic esters, such as epoxy-acrylates, urethane-acrylates or polyester acrylates.
24. Alkyd resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides.
26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.
27. Mixtures of polymers as mentioned above, for example PP/EPDM, Polyamide 6/EPDM or ABS, PVC/EVA, PVC/ABS, PVC/MBS, PC/ABS, PBTP/ABS.
28. Naturally occurring and synthetic organic materials which are pure monomeric compounds or mixtures of such compounds, for example mineral oils, animal and vegetable fats, oil and waxes, or oils, fats and wares based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.
29. Aqueous emulsions of natural or synthetic rubber, e.g. natural latex or lattices of carboxylated styrene/butadiene copolymers.
30. Polysiloxanes such as the soft, hydrophilic polysiloxanes described, for example, in U.S. Pat. No. 4,259,467; and the hard polyorganosiloxanes described, for example, in U.S. Pat. No. 4,355,147.
31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
32. Radiation curable compositions containing ethylenically unsaturated monomers or oligomers and a polyunsaturated aliphatic oligomer.
33. Epoxymelamine resins such as light-stable epoxy resins crosslinked by an epoxy functional coetherified high solids melamine resin such as LSE-4103 (Monsanto).

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants
1.1. Alkylated Monophenols, for Example,
2,6-di-tert-butyl-4-methylphenol,
2-tert.butyl-4,6-dimethylphenol,
2,6-di-tert-butyl-4-ethylphenol,
2,6-di-tert-butyl-4-n-butylphenol,
2,6-di-tert-butyl-4-i-butylphenol,
2,6-di-cyclopentyl-4-methylphenol,
2-(alpha-methylcyclohexyl)-4,6-dimethylphenol,
2,6-di-octadecyl-4-methylphenol,
2,4,6-tri-cyclohexylphenol,
2,6-di-tert-butyl-4-methoxymethylphenol.
1.2. Alkylated Hydroquinones, for Example,
2,6-di-tert-butyl-4-methoxyphenol,
2,5-di-tert-butyl-hydroquinone,
2,5-di-tert-amyl-hydroquinone,
2,6-diphenyl-4-octadecyloxyphenol.
1.3. Hydroxylated Thiodiphenyl Ethers, for Example,
2,2'-thio-bis-(6-tert-butyl-4-methylphenol),
2,2'-thio-bis-(4-octylphenol),
4,4'-thio-bis-(6-tert-butyl-3-methylphenol),
4,4'-thio-bis-(6-tert-butyl-2-methylphenol).
1.4. Alkylidene-Bisphenols, for Example,
2,2'-methylene-bis-(6-tert-butyl-4-methylphenol),
2,2'-methylene-bis-(6-tert-butyl-4-ethylphenol),
2,2'-methylene-bis-[4-methyl-6-(alpha.-methylcyclohexyl)-phenol],
2,2'-methylene-bis-(4-methyl-6-cyclohexylphenol),
2,2'-methylene-bis-(6-nonyl-4-methylphenol),
2,2'-methylene-bis-[6-[(.alpha.-methylbenzyl)-4-nonylphenol],
2,2'-methylene-bis46-(alpha.,.alpha.-dimethylbenzyl)-4-nonylphenol],
2,2'-methylene-bis-(4,6-di-tert-butylphenol),
2,2'-ethylidene-bis-(4,6-di-tert-butylphenol), 2,2'-ethylidene-bis-(6-tert-butyl-4-isobutylphenol),
4,4'-methylene-bis-(2,6-di-tert-butylphenol),
4,4'-methylene-bis-(6-tert-butyl-2-methylphenol),
1,1-bis-(5-tert-butyl-4-hydroxy-2-methylphenyl-butane,
2,6-di-(3-tert-butyl-5-methyl-2-hydroxybenzyl)-4-methylphenol,
1,1,3-tris-(5-tert-butyl-4-hydroxy-2-methylphenyl)-butane,
1,1-bis-(5-tert-butyl-4-hydroxy-2-methylphenyl)-3-n-dodecylmercaptobutane,
ethyleneglycol bis-[3,3-bis-(3'-tert-butyl-4'-hydroxyphenyl)-butyrate],
di-(3-tert-butyl-4-hydroxy-5-methylphenyl)-dicyclopentadiene,
di-[2-(3'-tert-butyl-2'-hydroxy-5'-methyl-benzyl)-6-ten-butyl-4-methylphenyl]terephthalate.

1.5. Benzyl Compounds, for Example,
1,3,5-tri-(3,5-di-tert-butyl-4-hydroxybenzyl)-2,4,6-trimethylbenzene,
di-(3,5-di-tert-butyl-4-hydroxybenzyl)sulfide,
3,5-di-tert-butyl-4-hydroxybenzyl-mercapto-acetic acid isooctyl ester,
bis-(4-tert-butyl-3-hydroxy-2,6-dimethylbenzyl)dithiol terephthalate,
1,3,5-tris-(3,5-di-tert-butyl-4-hydroxybenzyl)isocyanurate,
1,3,5-tris-(4-tert-butyl-3-hydroxy-2,6-dimethylbenzyl)isocyanurate,
3,5-di-tert-butyl-4-hydroxybenzyl-phosphoric acid dioctadecyl ester,
3,5-di-tert-butyl-4-hydroxybenzyl-phosphoric acid monoethyl ester, calcium-salt.

1.6. Acylaminophenols, for Example,
4-hydroxy-lauric acid anilide,
4-hydroxy-stearic acid anilide,
2,4-bis-octylmercapto-6-(3,5-tert-butyl-4-hydroxyanilino)-s-triazine,
octyl-N-(3,5-di-tert-butyl-4-hydroxyphenyl)-carbamate.

1.7. Amides of beta-(3,5-di-tert-butyl-4-hydroxyphenyl)-propionic acid for Example,
N,N'-di-(3,5-di-tert-butyl-4-hydroxyphenylpropionyl)-hexamethylenediamine,
N,N'-di-(3,5-di-tert-butyl-4-hydroxyphenylpropionyl)-trimethylenediamine,
N,N'-di-(3,5-di-tert-butyl-4-hydroxyphenylpropionyl)-hydrazine.

1.8. Diarylamines, for Example,
diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV Absorbers and Light Stabilizers 2.1. 2-(2'-Hydroxyphenyl)-benzotriazoles, for Example,
5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(.alpha.,.alpha.-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for Example,
4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of Optionally Substituted Benzoic Acids for Example,
phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for Example,
alpha-cyano-beta,beta-diphenylacrylic acid ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyanovinyl)-2-methyl-indoline.

2.5. Nickel Compounds, for Example,
nickel complexes of 2,2'-thio-bis-[4-(1,1,3,3-tetramethyl-butyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically Hindered Amines, for Example
bis-(2,2,6,6-tetramethylpiperidyl)sebacate, bis-(1,2,2,6,6-pentamethylpiperidyl)sebacate, n-butyl-3,5-di-tert-butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone).

2.7. Oxalic Acid Diamides, for Example,
4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixes of ortho- and para-methoxy- as well as of o- and p-ethoxy-disubstituted oxanilides.

2.8. Hydroxyphenyl-s-triazines, for Example
2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl-s-triazine; 2,4-bis[2-hydroxy-4-(2-hydroxy-4-(2-hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal Deactivators, for Example,
N,N'-diphenyloxalic acid diamide, N-salicylal-N'-salicyloyl-hydrazine, N,N'-bis-salicyloylhydrazine, N,N'-bis-(3,5-di-tert-butyl-4-hydroxyphenylpropionyl)hydrazine, 3-salicyloylamino-1,2,4-triazole, bis-benzylidene-oxalic acid dihydrazide.

4. Phosphites and Phosphonites, for Example,
triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl)phosphite, di-isodecyl-pentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which Destroy Peroxide, for Example, esters of beta-thiodipropionic acid, for example the lauryl, stearyl, myristyl or tridecyl esters, mercapto-benzimidazole or the zinc salt of 2-mercaptobenzimidazole, zinc dibutyldithiocarbamate, dioctadecyl disulfide, pentaerythritol tetrakis-(.beta.-dodecylmercapto)-propionate.

6. Hydroxylamines, for Example,

N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for Example,

N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide Stabilizers, for Example copper salts in combination with iodides and/or phosphorus compounds and salts of divalent manganese.

9. Basic Co-Stabilizers, for Example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating Agents, for Example, 4-tert-butyl-benzoic acid, adipic acid, diphenylacetic acid.

11. Fillers and Reinforcing Agents, for Example, calcium carbonate, silicates, glass fibers, asbestos, talc, kaolin, mica, barium sulfate, metal oxides and hydroxides, carbon black, carbon nanotubes, graphite.

12. Other Additives, for Example, plasticizers, lubricants, emulsifiers, pigments, optical brighteners, flameproofing agents, anti-static agents, blowing agents and thiosynergists such as dilauryl thiodipropionate or distearyl thiodipropionate.

Phenolic antioxidants are of particular interest and preferably selected from the group consisting of n-octadecyl 3,5-di-tert-butyl-4-hydroxyhydrocinnamate, neopentanetetrayl tetrakis(3,5-di-tert-butyl-4-hydroxyhydrocinnammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocyanurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-tri-methyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis (4,6-di-tert-butylphenol).

Further, the compositions according to the instant invention may additionally contain a hindered amine.

The hindered amine compound of particular interest is selected from the group consisting of bis(2,2,6,6-tetramethylpiperidin-4-yl)sebacate, bis(1,2,2,6,6-pentamethylpiperidin-4-yl)sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl)nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2]heneicosane, polycondensation product of 2,4-dichloro-6-tert-octylamino-s-triazine and 4,4'-hexamethylenebis (amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis (amino-2,2,6,6-tetramethylpiperidine), N,N',N",N'"-tetrakis [(4,6-bis(butyl-2,2,6,6-tetramethyl-piperidin-4-yl)-amino-s-triazin-2-yl]-1,10-diamino-4,7-diazadecane, mixed [2,2,6,6-tetramethylpiperidin-4-yl/.beta.,.beta.,.beta.',.beta.'-tetramethyl-3,9-(2,4,8,10-tetraoxaspiro[5.5]-undecane) diethyl]1,2,3,4-butanetetracarboxylate, mixed [1,2,2,6,6-pentamethylpiperidin-4-yl/.beta.,.beta.,.beta.',.beta.'-tetramethyl-3,9-(2,4,8,10-tetraoxaspiro[5.5]-undecane) diethyl]1,2,3,4-butanetetracarboxylate, octamethylene bis(2,2,6,6-tetramethylpiperidin-4-carboxylate), 4,4'-ethylenebis (2,2,6,6-tetramethylpiperazin-3-one), N-2,2,6,6-tetramethylpiperidin-4-yl-n-dodecylsuccinimide, N-1,2,2,6,6-pentamethylpiperidin-4-yl-n-dodecylsuccinimide, N-1-acetyl-2,2,6,6-tetramethylpiperidin-4-yln-dodecylsuccinimide, 1-acetyl3-dodecyl-7,7,9,9-tetramethyl-1,3,8-triazaspiro[4.5]decane-2,4-dione, di-(1-octyloxy-2,2,6,6-tetramethylpiperidin-4-yl)sebacate, di-(1-cyclohexyloxy-2,2,6,6-tetramethylpiperidin-4-yl)succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], and 2,4,6-tris[N-(1-cyclohexyloxy-2,2,6,6-tetramethylpiperidin-4-yl)-n-butylamino]-s-triazine.

A most preferred hindered amine compound is bis(2,2,6,6-tetramethylpiperidin-4-yl)sebacate, bis(1,2,2,6,6-pentamethylpiperidin-4-yl)sebacate, di(1,2,2,6,6-pentamethylpiperidin-4-yl) (3,5-di-tert-butyl-4-hydroxybenzyl) butylmalonate, the polycondensation product of 1-(2- hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis(amino-2,2,6,6-tetramethylpiperidine), N,N',N'',N'''-tetrakis[(4,6-bis(butyl-(2,2,6,6-tetramethyl-piperidin-4-yl)amino)-s-triazine-2-yl]-1,10-diamino-4,7-diazadecane. di-(1-octyloxy-2,2,6,6-tetramethylpiperidin-4-yl)sebacate, di-(1-cyclohexyloxy-2,2,6,6-tetramethylpiperidin-4-yl)succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl(imino], or 2,4,6-tris[N-(1-cyclohexyloxy-2,2,6,6-tetramethylpiperidin-4-yl)-n-butylamino]-s-triazine.

Cosmetics and Personal Care

In one main aspect, the present invention relates to a cosmetic and personal care preparation or formulation e.g. comprising (a) a (cosmetically) suitable carrier material, and
(b) a compound of formula (I) as explained above.

The present invention provides a cosmetic composition which exhibits at least one of the following effects, for example aesthetic, goniochromatic, and volume effects. Such effects may be obtained by use of compositions, for example, chosen from foundations, eye shadows, blushes, lipsticks, lip glosses, lip lacquers, mascaras, and eyeliners.

The preparations according to the invention are especially preparations or formulations that are suitable for making-up the lips or the skin and for colouring the hair or the nails. The cosmetic preparations are, for example, lipsticks, blushers, foundations, nail varnishes and hair shampoos.

The composition according to the present invention may also contain one or one more additional compounds as described below.

Fatty alcohols
Esters of fatty acids
Natural or synthetic triglycerides including glyceryl esters and derivatives
Waxes including esters of long-chain acids and alcohols as well as compounds having wax-
Hydrocarbon oils
Silicones or siloxanes
Fluorinated or perfluorinated oils,
Super-fatting agents,
Pearlescent waxes,
Anti-wrinkle actives,
Skin lightening agents,
Deodorising active ingredients,
Consistency regulators/thickeners—Rheology modifiers, such as Natural thickeners, Mineral thickeners, Synthetic Rheology modifiers, Phospholipid derivatives;
Polymers, e.g. cationic polymers such as cationic cellulose derivatives, anionic, zwitterionic, amphoteric and non-ionic polymers;
Hydrotropic agents,
Perfume oils,
Emulsifiers, such as O/W emulsifiers, W/O emulsifiers, Non ionic emulsifiers such as PEG modified components, Anionic emulsifiers, Silicone emulsifiers (particularly suitable for W/Si emulsions);
see corresponding components published on Oct. 25, 2005 on ip.com under the identifier IPCOM000130489D for further details.

Further components useful in the present cosmetic, personal care or dermatological formulations are as listed in WO04/20530, page 2 line 16 until page 18 line 3, including gloss pigments and their use as disclosed from page 24, line 1, until page 37, line 8 of said document, which passages are hereby incorporated by reference.

The compounds described herein may also be used to protect human or animal skin and hair from UV radiation and the deleterious effects of radicals and/or oxidants. The present invention therefore also relates to dermatological and cosmetic compositions comprising such compounds. In a particular embodiment, the instant invention also relates to cosmetic compositions intended for make-up comprising a compound of general formula (I) wherein said cosmetic composition is preferably in the form of foundation, pressed powder, face powder, lipstick, eye shadow, eyebrow pencil, eye liner, mascara, anhydrous or hydrated emulsion, and paste and wherein said cosmetic composition additionally comprises cosmetically acceptable ingredients which include oils, waxes, surfactants, silicones, perfluorides, synthetic organic UV-absorbers, fragrances or other materials listed in INCI (International Nomenclature of Cosmetic Ingredients).

The cosmetic composition may also contain non-coated or differently coated powder, as well as nacres and/or fillers, and also pigments that are well known in the art. The nacres may be present in the composition in a proportion of from 0 to 20% by weight and preferably from 8% to 15% by weight, and may be chosen from natural mother-of-pearl, mica coated with titanium oxide, with iron oxide, with natural pigment or with bismuth oxychloride, and also coloured titanium mica. The fillers, which may be present in a proportion of from 0 to 30% by weight and preferably from 5% to 15%, in the composition, may be mineral or synthetic, and lamellar or non-lamellar. Mention may be made of talc, silica, kaolin, nylon powder, PE powder, Teflon, starch, boron nitride, polymer microspheres, silicone microbeads, muscovite, sericite, Mg and Ca carbonate, silicates, clay, BiOCl, or beads of a polymeric material and metal soaps, as well as other treated or untreated pigments.

Typical make-up compositions are eye shadow pencils, mascara, eye shadow powder compacts, liquid compositions for eye shadow and eye makeup, lipsticks and lip gloss, make-up in pencil form, make-up powder compacts, make-up emulsions, make-up gel, foam bath concentrates with color gloss, skin care lotions, sun-protecting emulsions and lotions.

The composition may also comprise a water-soluble or liposoluble colorant, especially a natural organic colorant such as cochineal carmine, and/or a synthetic colorant such as halo acid, azo or anthraquinone dyes, and further natural dyes and pigments including carotenoids, xanthophyll, caramel, vegetal charcoal (Carbo vegetabilis), and melanins. The invention also refers to the use of pigments in pharmaceutical or food manufacturing and in agriculture, e.g. seed coating/coloring. Finally, the inventive pigments may be also be applied in industrial application, thereby including: coatings and inks (appliance and architectural coatings, automotive refinishing, custom finishing, industrial coating); leather coating; electronic product housings, plastics and rubber (toys and sporting goods, plastic packaging); textile coatings and inks.

Yet another embodiment of the instant invention relates to a dermatological, pharmaceutical or food product comprising a compound of general formula (I).

Finally, the instant invention also pertains to the use of a compound of general formula (I)

25

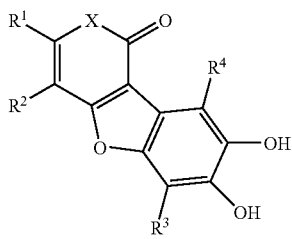

(I)

wherein

X is O, NH or NR$^{15}$,

R$^1$, R$^2$, R$^3$ and R$^4$ are independently of each other H, halogen, especially fluorine, hydroxy, C$_1$-C$_{24}$alkyl, C$_1$-C$_{24}$alkyl which is substituted by at least one E and/or interrupted by at least one D, C$_1$-C$_{24}$ perfluoroalkyl, C$_6$-C$_{14}$ perfluoroaryl, especially pentafluorophenyl, C$_5$-C$_{12}$cycloalkyl, C$_5$-C$_{12}$cycloalkyl which is substituted by G and/or interrupted by S—, —O—, or —NR$^{15}$—, —NR$^{15}$R$^{16}$, C$_1$-C$_{24}$alkylthio, —PR$^{17}$R$^{18}$, C$_5$-C$_{12}$cycloalkoxy, C$_5$-C$_{12}$cycloalkoxy which is substituted by G, C$_6$-C$_{24}$aryl, C$_6$-C$_{24}$aryl which is substituted by G, C$_1$-C$_{24}$alkyl, C$_5$-C$_{12}$cycloalkyl, C$_7$-C$_{25}$aralkyl, C$_1$-C$_{24}$ perfluoroalkyl, C$_6$-C$_{14}$ perfluoroaryl, especially pentafluorophenyl, or C$_1$-C$_{24}$haloalkyl; C$_2$-C$_{20}$heteroaryl, C$_2$-C$_{20}$heteroaryl which is substituted by G, fluorine, C$_1$-C$_{24}$alkyl, C$_5$-C$_{12}$cycloalkyl, C$_7$-C$_{25}$aralkyl, C$_1$-C$_{24}$ perfluoroalkyl, C$_6$-C$_{14}$perfluoroaryl, especially pentafluorophenyl, or C$_1$-C$_{24}$haloalkyl; C$_2$-C$_{24}$alkenyl, C$_2$-C$_{24}$alkynyl, C$_1$-C$_{24}$alkoxy, C$_1$-C$_{24}$alkoxy which is substituted by at least one E and/or interrupted by at least one D, C$_7$-C$_{25}$aralkyl, C$_7$-C$_{25}$aralkyl, which is substituted by G, C$_7$-C$_{25}$aralkoxy, C$_7$-C$_{25}$aralkoxy which is substituted by G, or —CO—R$^{19}$, or R$^1$ and R$^2$ are a group

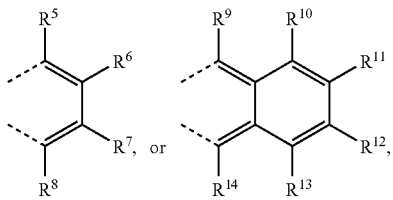

wherein R$^5$, R$^6$, R$^7$, R$^8$, R$^9$, R$^{10}$, R$^{11}$, R$^{12}$ and R$^{14}$ are independently of each other H, halogen, hydroxy, C$_1$-C$_{24}$alkyl, C$_1$-C$_{24}$alkyl which is substituted by at least one E and/or interrupted by at least one D, C$_1$-C$_{24}$ perfluoroalkyl, C$_6$-C$_{14}$perfluoroaryl, especially pentafluorophenyl, C$_5$-C$_{12}$cycloalkyl, C$_5$-C$_{12}$cycloalkyl which is substituted by at least one G and/or interrupted by at least one S—, —O—, or —NR$^{15}$—, C$_5$-C$_{12}$cycloalkoxy, C$_5$-C$_{12}$cycloalkoxy which is substituted by G, C$_6$-C$_{24}$aryl, C$_6$-C$_{24}$aryl which is substituted by at least one G, C$_2$-C$_{20}$heteroaryl, C$_2$-C$_{20}$heteroaryl which is substituted by at least one G, C$_2$-C$_{24}$alkenyl, C$_2$-C$_{24}$alkynyl, C$_1$-C$_{24}$alkoxy, C$_1$-C$_{24}$alkoxy which is substituted by at least one E and/or interrupted by at least one D, C$_7$-C$_{25}$aralkyl, C$_7$-C$_{25}$aralkyl, which is substituted by at least one G, C$_7$-C$_{25}$aralkoxy, C$_7$-C$_{25}$aralkoxy which is substituted by at least one G, or at least —CO—R$^{19}$, D is —CO—; —COO—; —S—; —SO—; —SO$_2$—; —O—; —NR$^{25}$—; —POR$^{17}$—; —CR$^{20}$=CR$^{21}$—; or —C≡C—;

26

E is —OR$^{22}$; —SR$^{22}$; —NR$^{15}$R$^{16}$; —[NR$^{15}$R$^{16}$R$^{24}$]$^+$Z$^-$; —COR$^{19}$; —COOR$^{23}$; —CONR$^{15}$R$^{16}$; —CN; —N$_3$; —OCOOR$^{23}$; or halogen; and G is E, or C$_1$-C$_{24}$alkyl, wherein R$^{20}$, R$^{21}$, R$^{15}$, R$^{16}$ and R$^{24}$ are independently of each other H; C$_6$-C$_{18}$aryl; C$_6$-C$_{18}$aryl which is substituted by C$_1$-C$_{24}$alkyl, or C$_1$-C$_{24}$alkoxy; C$_1$-C$_{24}$alkyl; or C$_1$-C$_{24}$alkyl which is interrupted by at least one —O—; or R$^{15}$ and R$^{16}$ together form a five or six membered ring, in particular

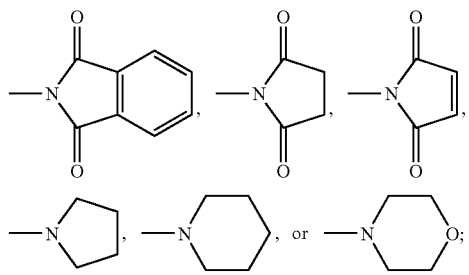

Z is halogen, preferably Cl;

R$^{19}$ and R$^{23}$ are independently of each other H; C$_6$-C$_{18}$aryl; C$_6$-C$_{18}$aryl which is substituted by C$_1$-C$_{24}$alkyl, or C$_1$-C$_{24}$alkoxy; C$_1$-C$_{24}$alkyl; or C$_1$-C$_{24}$alkyl which is interrupted by at least one —O—;

R$^{22}$ is H; C$_6$-C$_{18}$aryl; C$_6$-C$_{18}$aryl, which is substituted by C$_1$-C$_{24}$alkyl, or C$_1$-C$_{24}$alkoxy; C$_1$-C$_{24}$alkyl; or C$_1$-C$_{24}$alkyl which is interrupted by at least one —O—; and R$^{17}$ and R$^{18}$ are independently of each other C$_1$-C$_{24}$alkyl, C$_6$-C$_{18}$aryl, or C$_6$-C$_{18}$aryl, which is substituted by C$_1$-C$_{24}$alkyl;

R$^3$ and/or R$^4$ may further be a mono-, di- or oligosaccharide residue alpha- or beta-linked to the phenolic ring system either directly or via the phenolic oxygen;

for enhancing the photostability of cosmetic or dermatologic compositions (optionally comprising at least one further organic UV absorber).

Preferably, the compound of general formula (I) is used in amounts from 0.001 to 20% by weight, preferably from 0.01 to 2% by weight in the cosmetic or dermatological sun screen formulations. The cosmetic or dermatological formulation comprises further organic UV absorbers selected from cinnamic acid derivatives and di benzoyl methane derivatives, preferably selected from isopentyl p-methoxycinnamate, 2-ethylhexyl 4-methoxycinnamate and ethylhexyl methoxycinnamate.

The present invention also relates to the use of the compound of general formula (I) described hereinbefore for stabilizing oxidation-sensitive and/or UV-sensitive active ingredients or for protecting human or animal skin and hair from UV radiation and the deleterious effects of radicals and/or oxidants.

The following examples are presented for the purpose of illustration only and are not to be construed to limit the nature or scope of the instant invention in any manner whatsoever.

EXAMPLES

Example 1

Laccase-Catalysed Synthesis of the Compound A-2 of Formula (1)

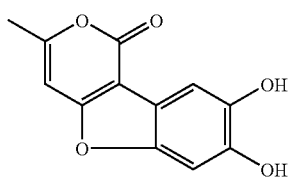 [SMILES: Cc1cc2oc3cc(O)c(O)cc3c2c(=O)o1]

(1)

The compound of formula (1) is obtained from commercial pyrocatechol (Merck) and 4-hydroxy-6-methyl-2-pyrone (Alfa Aesar). 1.26 g of 4-hydroxy-6-methyl-2-pyrone are dissolved in 100 mL of sodium acetate buffer (0.025 mM; pH 4.65) and 80 mL of ethanol. 1.10 g of pyrocatechol are dissolved in 100 mL of the aforementioned buffer. Subsequently both solutions are mixed together in a 1-L Erlenmeyer flask and 1 mL of the enzyme stock is added. The enzyme stock is prepared by solubilisation of 10 mg of the lyophilized enzyme (laccase from *Trametes versicolor*, Fluka) in 10 mL of the aforementioned buffer. The reaction mixture is vigorously stirred for several hours until reaction end is indicated by missing pyrocatechol in TLC. The reaction mixture is filtered and the filter residue recrystallised from methanol and acetone. A slightly pink solid is obtained (1.65 g) corresponding to formula (1).

$^1$H-NMR (DMSO, 300 MHz): 9.38; 9.31; 7.15; 7.07; 6.86 (d); 3.32; 2.33

$^{13}$C-NMR (DMSO, 75 MHz): 20.6; 96.6; 99.6; 103.6; 105.4; 113.9; 144.9; 146.3; 149.1; 159.5; 161.8; 163.7;

UV-Vis (MeOH): $\lambda_{max}$=332 nm, E=16982.

Example 2

Laccase-Catalysed Synthesis of the Compound A-1 of Formula (2)

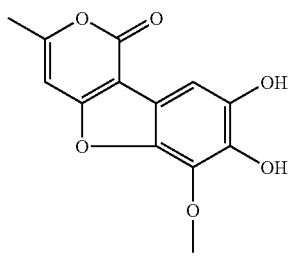 [SMILES: COc1c(O)c(O)cc2c1oc1cc(C)oc(=O)c12]

(2)

The compound of formula (2) is obtained from commercial 3-methoxypyrocatechol (Merck) and 4-hydroxy-6-methyl-2-pyrone (Alfa Aesar). 1.26 g of 4-hydroxy-6-methyl-2-pyrone are dissolved in 100 mL of sodium acetate buffer (0.025 mM; pH 4.65) and 80 mL of ethanol. 1.40 g of pyrocatechol are dissolved in 100 mL of the aforementioned buffer. Subsequently both solutions are mixed together in a 1-L Erlenmeyer flask and 1 mL of the enzyme stock is subsequently added. The enzyme stock is prepared by solubilisation of 10 mg of the lyophilized enzyme (laccase from *Trametes versicolor*, Fluka) in 10 mL of the aforementioned buffer. The reaction mixture is vigorously stirred for several hours until reaction end is indicated by missing the diphenol in TLC. The reaction mixture is filtered and the filter residue recrystallized from methanol and acetone affording a slightly orange-brown solid (0.62 g) corresponding to formula (2).

$^1$H-NMR (DMSO, 300 MHz): 9.45; 8.91; 6.92 (d); 6.89; 3.33; 2.33;

$^{13}$C-NMR (DMSO, 75 MHz): 163.8; 162.1; 159.5; 146.1; 141.5; 138.1; 134.2; 114.3; 103.6; 99.9; 96.6; 61.3; 20.7;

UV-Vis (MeOH): $\lambda_{max}$=330 nm, E=14696.

Example 3

Laccase-Catalysed Synthesis of the Compound B-2 of Formula (3)

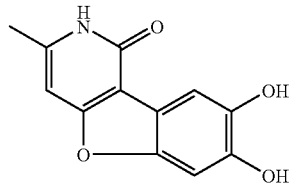

(3)

The compound of formula (3) is obtained from commercial pyrocatechol (Merck) and 2,4-dihydroxy-6-methylpyridine (Acros). 3.12 g of 2,4-dihydroxy-6-methylpyridine are dissolved in 250 mL of sodium acetate buffer (0.025 mM; pH 4.65) and 125 mL of dimethylacetamide under heat. 2.75 g of pyrocatechol are dissolved in 250 mL of the aforementioned buffer. Subsequently both solutions are mixed together in a 1-L Erlenmeyer flask and 1.5 mL of the enzyme stock is added. The enzyme stock is prepared by solubilisation of 10 mg of the lyophilized enzyme (laccase from *Trametes versicolor*, Fluka) in 10 mL of the aforementioned buffer. The reaction mixture is vigorously stirred for several hours until reaction end is indicated by missing pyrocatechol in TLC. The reaction mixture is filtered and a dark-brown solid is obtained (1.27 g) corresponding to formula (3).

$^1$H-NMR (DMSO, 300 MHz): 11.50 (NH); 9.10 (OH); 7.28; 6.99; 6.43 (d); 2.27;

$^{13}$C-NMR (DMSO, 75 MHz): 162.8; 160.2; 148.8; 145.3; 143.9; 143.8; 115.4; 108.7; 106.2; 99.2; 94.2; 19.7;

UV-Vis (MeOH): $\lambda_{max}$=331 nm, $\epsilon$=24746.

Example 4

Example 4.1

Synthesis of the Compound of Formula (4)

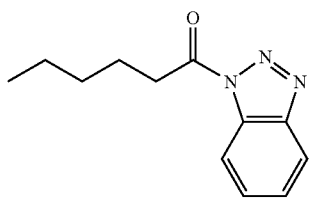

(4)

The compound of formula (4) is obtained from commercial hexanoyl chloride (Fluka) and 1H-benzotriazole (Fluka). 96 g of 1H-benzotriazole are dissolved in 1000 mL of dichloromethane. Subsequently 108 g of hexanoyl chloride are added. The mixture is cooled on ice and finally 81 g of triethylamine are added. The reaction mixture is vigorously stirred over night at room temperature. After the reaction is completed, the mixture is twice extracted with 1 L of H$_2$O (aqueous phase discarded). The organic phase is washed with 1 L of saturated NaHCO$_3$ (aqueous phase discarded), dried over Na$_2$SO$_4$ and the solvent removed under reduced pressure affording a slightly yellow oil (155 g).

$^1$H-NMR (CDCl3, 300 MHz): 8.29 (t); 8.26 (t); 8.11 (t); 8.08 (t); 7.65 (d); 7.63 (t); 7.60 (d); 7.51 (d); 7.48 (t); 7.45 (d); 7.24; 3.44-3.38 (t); 1.97-1.87 (q); 1.53-1.34; 0.96-0.91 (t);

$^{13}$C-NMR (CDCl3, 75 MHz): 172.8; 146.3; 131.3; 130.5; 126.2; 120.3; 114.7; 35.8; 31.6; 24.5; 22.7; 14.2.

Example 4.2

Synthesis of the Compound of Formula (5)

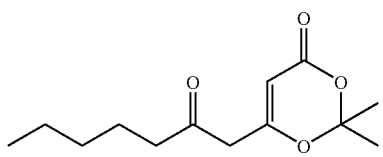

(5)

The compound of formula (5) is obtained from commercial 2,2,6-trimethyl-3-dioxinon-4-one (Fluka; distilled before use) and compound of formula (4) via lithium diisopropylamide mediated deprotonation and alkylation (Katritzky et al., 2005). To a mixture of 3.85 g of diisopropylamine in 100 mL of THF 64.1 mL of n-butyllithium (1.6 M in n-hexane) are added dropwise within 30 min at −78° C. Subsequently a solution of 4.49 g of 2,2,6-trimethyl-3-dioxinon-4-one in 100 mL of THF is added dropwise within 10-15 min at −78° C. and the mixture stirred for 1.5 h. Subsequently 5.43 g of the compound of formula (4) are dissolved in 100 mL of THF and added dropwise at −78° C. The stirred reaction mixture warms up to room temperature overnight. The reaction is quenched by the addition of 10 mL of a saturated solution of NH$_4$Cl. The reaction mixture is washed with 500 mL of H$_2$O and 250 mL of ethyl acetate and the aqueous phase again extracted twice with ethyl acetate (each time 250 mL). The aqueous phase is finally discarded and the organic phases are combined. The resulting organic phase is washed with 750 mL of saturated solution of NaHCO$_3$, with 500 mL of a saturated solution of NaCl and finally dried over anhydrous Na$_2$SO$_4$. The solvent is removed under reduced pressure and the crude product purified by column chromatography on silica gel using n-hexane and ethyl acetate as eluent (1/1, v/v) in the beginning and methanol at the end affording a dark yellow high viscous oil (2.5 g).

$^1$H-NMR (CDCl3, 300 MHz): 5.32; 3.30; 2.50-2.45 (t); 2.37-2.31 (t); 1.97 (d); 1.70; 1.67; 1.26; 0.90-0.85 (t).

Example 4.3

Synthesis of the Compound of Formula (6)

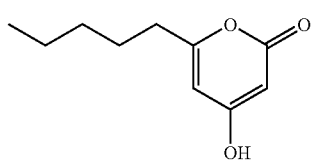

(6)

The compound of formula (6) is obtained from the compound of formula (5) by thermal cyclization. 2.0 g of the compound of formula (5) are dissolved in toluene and heated under reflux for 2 h. After the reaction is completed, the solvent is removed by evaporation and the crude product is purified by column chromatography with n-hexane/ethyl acetate as eluent (10/1 v/v) affording a yellowish high viscous oil (1.4 g).

$^1$H-NMR (CDCl3, 300 MHz): 5.91; 5.63; 3.47; 2.41-2.33 (t); 1.60-1.50 (q); 1.30-1.23;

$^{13}$C-NMR (CDCl3, 75 MHz): 168.7; 166.9; 102.4; 90.5; 50.8; 33.8; 31.5; 26.7; 22.6; 14.2.

Example 4.4

Laccase-Mediated Synthesis of the Compound A-10 of Formula (7)

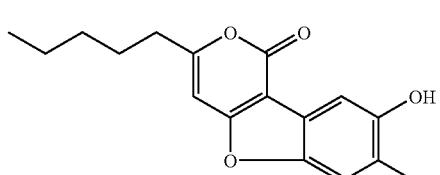

(7)

The compound of formula (7) is obtained from commercial pyrocatechol (Merck) and compound of formula (6). 490 mg of the compound of formula (6) are dissolved in 50 mL of Na-acetate buffer (0.025 mM; pH 4.65) and 20 mL of dimethylformamide under heating. This solution was mixed together with a solution of 275 mg of pyrocatechol in 50 mL of the aforementioned buffer. Subsequently 300 µL of the enzyme stock solution are added. The enzyme stock is prepared by dissolution of 10 mg of the lyophilized enzyme (laccase from *Trametes versicolor*, Fluka) in 10 mL of the aforementioned buffer. The reaction mixture is vigorously stirred for several hours until reaction end is indicated by missing pyrocatechol in TLC. The reaction mixture is filtered. A slightly brown solid is obtained (100 mg) corresponding to formula (7).

$^1$H-NMR (DMSO, 300 MHz): 9.40; 9.31; 7.16; 7.07; 6.90; 3.29; 2.62-2.58 (t); 1.68-1.59 (t); 1.34-1.27; 0.89-0.84.

Example 5

Example 5.1

Synthesis of the Compound of Formula (8)

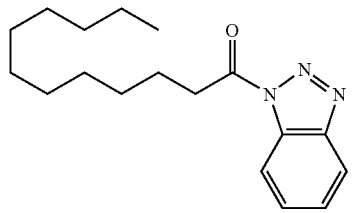

(8)

The compound of formula (8) is obtained from commercial lauryl chloride (Fluka) and 1H-benzotriazole (Fluka). 73 g of 1H-benzotriazole are dissolved in 1000 mL of dichloromethane. Subsequently 133 g of lauryl chloride are added. The reaction mixture is cooled on ice and finally 61 g of triethylamine are added. The reaction mixture is vigorously stirred over night. After reaction is completed the product is extracted with 1 L of $H_2O$ two times (aqueous phase discarded). The organic phase is washed with 1 L of saturated $NaHCO_3$ (aqueous phase discarded), dried over $Na_2SO_4$ and concentrated under reduced pressure. Slightly yellow oil is obtained (150 g).

$^1$H-NMR (CDCl3, 300 MHz): 8.29 (t); 8.27 (t); 8.11 (t); 8.08 (t); 7.65 (d); 7.62 (t); 7.60 (d); 7.50 (d); 7.48 (t); 7.45 (d), 3.43-3.39 (t); 1.96-1.86 (qui); 1.51-1.26 (chain); 0.90-0.85 (t);

$^{13}$C-NMR (CDCl3, 75 MHz): 172.8; 146.4; 131.3; 130.5; 126.2; 120.3; 114.7; 35.9; 32.3; 29.9; 29.8; 29.7; 29.6; 29.5; 24.9; 23.0; 14.5.

Example 5.2

Synthesis of the Compound of Formula (9)

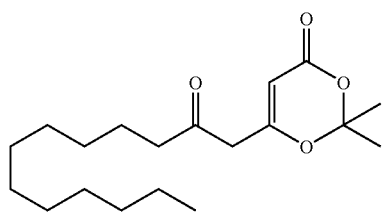

(9)

The compound of formula (9) is obtained from commercial 2,2,6-trimethyl-3-dioxinon-4-one (Fluka; distilled before use) and compound of formula (8) via lithium diisopropylamide mediated deprotonation and alkylation (Katritzky et al., 2005). 3.85 g of diisopropylamine are added to 100 mL of THF at −78° C. Subsequently 64.1 mL of n-butyllithium (1.6 M in n-hexane) are added dropwise within 30 min. Subsequently 4.49 g of 2,2,6-trimethyl-3-dioxinon-4-one in 100 mL of THF are added dropwise within 10-15 min at −78° C. and the mixture is stirred for 1.5 h. Subsequently 7.54 g of the compound of formula (8) are dissolved in 100 mL of THF and added dropwise at −78° C. The stirred reaction mixture warms up to room temperature overnight. The reaction is quenched by the addition of 10 mL of a saturated solution of $NH_4Cl$. Then the reaction mixture is extracted with 500 mL of $H_2O$ and 250 mL of ethyl acetate and the aqueous phase again extracted twice with ethyl acetate (each time 250 mL). The aqueous phase is finally discarded. The combined organic phases are extracted with 750 mL of saturated solution of $NaHCO_3$ and finally with 500 mL of a saturated solution of NaCl. The solvent was removed with a rotary evaporator and the crude product purified by flash chromatography (n-hexane and ethyl acetate 1:1 in the beginning and methanol at the end) affording a yellow high viscous oil (3.32 g).

$^1$H-NMR (CDCl3, 300 MHz): 5.32; 3.30; 2.51-2.45 (t); 1.71; 1.65-1.55 (q); 1.33-1.25; 0.92-0.87 (t).

Example 5.3

Synthesis of the Compound of Formula (10)

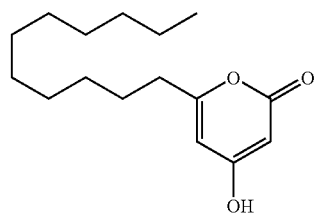

(10)

The compound of formula (10) is obtained from the compound of formula (9) by thermal cyclization. 3.3 g of the compound of formula (5) are dissolved in toluene and heated under reflux for 2 h. After the reaction is completed, the solvent is removed by evaporation and the crude product is purified by flash chromatography (n-hexane/ethyl acetate 10:1) affording a yellowish high viscous oil (2.5 g).

$^1$H-NMR (CDCl3, 300 MHz): 5.86; 5.52; 2.36 (t); 1.54; 1.24; 0.90-0.85 (t).

$^{13}$C-NMR (CDCl3, 75 MHz): 168.85; 166.71; 102.71; 90.38; 33.89; 32.28; 30.05; 30.02; 29.95; 29.73; 29.51; 27.04; 23.05; 14.47.

Example 5.4

Laccase-Mediated Synthesis of the Compound A-28 of Formula (11)

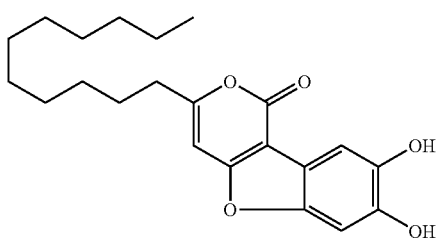

(11)

The compound of formula (11) is obtained from commercial pyrocatechol (Merck) and compound of formula (10). 665 mg of the compound of formula (10) are dissolved in 50 mL of Na-acetate buffer (0.025 mM; pH 4.65) and 50 mL of dimethylformamide under heating. This solution was mixed together with a solution of 275 mg of pyrocatechol in 50 mL of the aforementioned buffer and 300 μL of the enzyme stock solution are added. The enzyme stock is prepared by solubilisation of 10 mg of the lyophilized enzyme (laccase from *Trametes versicolor*, Fluka) in 10 mL of the aforementioned buffer. The reaction mixture is then vigorously stirred for several hours until reaction end is indicated by missing pyrocatechol in TLC. The reaction mixture is filtered affording a slightly brown solid (267 mg) corresponding to formula (11).

$^1$H-NMR (DMSO, 300 MHz): 7.16; 7.07; 6.90; 5.90; 5.18; 3.29; 2.88; 2.72; 2.43-2.38 (t); 1.58-1.46 (t); 1.23; 0.86-0.82 (q).

Example 6

Synthesis of the Compounds A-11, A-19 and A-23

6.1: Compound A-23

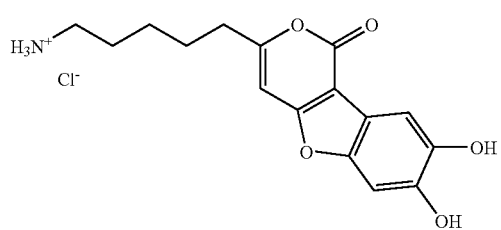

(A-23)

0.55 g of compound A-11 are dissolved in 50 ml of diethylether containing 2.5 molar gaseous hydrogen chloride at room temperature. The mixture is stirred for 30 minutes and subsequently evaporated to dryness to leave 0.58 g of A(23) as slightly brown amorphous mass.

$^1$H-NMR (CD$_3$OD, 300 MHz): 7.26 (s, 1H); 7.10 (s, 1H); 6.76 (s, 1H); 2.98 (t, 2H); 2.70 (t, 2H); 1.67-1.82 (m, 4H); 1.42-1.52 (m, 2H).

6.2: Compound A-11

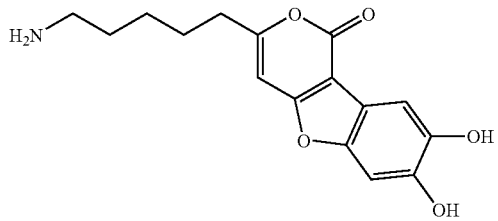

(A-11)

0.98 g of compound azide A-19 are dissolved in 10 ml dry methanol under an argon atmosphere at room temperature. To this mixture are added 15.5 mg catalyst (10% Pd on charcoal, Fluka) and the slurry is vigorously stirred. Hydrogen gas is bubbled through the solution until complete consumption of the azide. The mixture subsequently is purged with nitrogen, filtered over celite and evaporated to dryness to give 0.58 g of the amine A-11 as a beige powder.

$^1$H-NMR (CD$_3$OD, 300 MHz): 7.36 (s, 1H); 7.07 (s, 1H); 6.64 (s, 1H); 2.92 (t, 2H); 2.70 (t, 2H); 1.66-1.86 (m, 4H); 1.44-1.54 (m, 2H).

6.3: Compound A-19

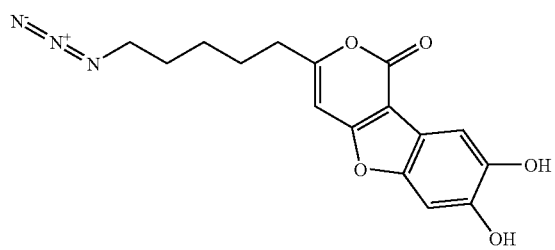

(A-19)

1.96 of azide (21), 0.88 g of commercial 1,2-dihydroxy benzene (Fluka) are dissolved in a 1/1 (v/v) mixture of ethanol and water and vigorously stirred in an open beaker. To this mixture is then added 1 ml of a laccase solution (*Trametes versicolor*, Fluka, 10 mg in 10 ml Na-acetate buffer (0.025 mM; pH 4.65). The mixture is vigorously stirred for two days at room temperature. The product is then recovered by filtration. 1.1 g of A-19 are obtained as a slightly yellow solid.

$^1$H-NMR (CD$_3$OD, 300 MHz): 7.34 (s, 1H); 7.08 (s, 1H); 6.56 (s, 1H); 3.31 (t, 2H); 2.67 (t, 2H); 1.79 (quin., 2H); 1.65 (quint., 2H); 1.49 (quint., 2H). IR: strong band at 2100 cm$^{-1}$.

6.4: Intermediate Compound 21

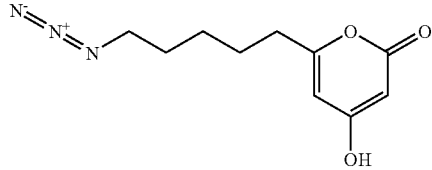

(21)

6.74 g of compound (22) are dissolved in 180 ml of toluene under an argon atmosphere and to 120° C. for about 45 minutes until the starting material has been consumed. The solvent is then evaporated under reduced pressure and the resulting residue purified over a silica gel column (eluent: hexane/ethyl acetate: 4/1 to 0/1) to give the compound (21) as yellow solid.

$^1$H-NMR (CD$_3$OD, 300 MHz): 5.96 (broad s, 1H); 5.57 (d, 1H); 3.27 (t, 2H); 2.507 (t, 2H); 1.69 (quin., 2H); 1.63 (quintet, 2H); 1.43 (quint., 2H). IR: strong band at 2100 cm$^{-1}$.

6.5: Intermediate Compound 22

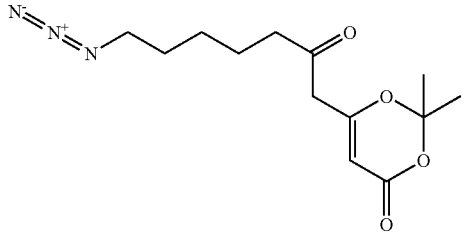

(22)

5.50 g of dry di-isopropyl amine are dissolved in 150 ml dry THF under an argon atmosphere and cooled to –78° C. To this mixture are dropped within 5 minutes 22 ml of a 2.7 molar solution of butyl lithium in heptane (Fluka) and stirred for an additional 30 minutes at that temperature. To the resulting LDA solution is then dropped a solution of 6.04 g 2,2,6-trimethyl-4H-1,3-dioxin-4-on (Fluka), dissolved in 150 ml of dry THF within one hour. At –78° C. is then finally added a solution of 9.40 g of compound (23) dissolved in 150 ml THF within one hour. The resulting solution is then stirred and reaches gradually room temperature within about 10 hours. The solvent is then evaporated and the residue dissolved in ethyl acetate and subsequently extracted with water and brine. The organic phase is dried over sodium sulphate, filtered and evaporated. The resulting red oil is purified over a silica gel column (eluent: hexane/ethyl acetate: 4/1) to yield 6.74 g of compound (22) as a slightly yellow oil.

$^1$H-NMR (CD$_3$OD, 300 MHz): 5.33 (s, 1H); 3.31 (s, 2H); 3.28 (t, 2H); 2.52 (t, 2H); 1.71 (s, 6H); 1.56-1.68 (m, 4H); 1.35-1.44 (m, 2H). IR: strong band at 2100 cm$^{-1}$.

6.6: Intermediate Compound 23

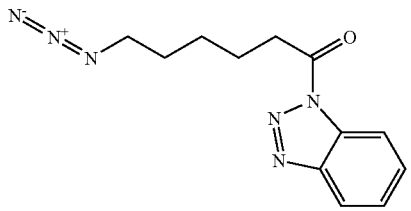

(23)

47.9 g of compound (24) are dissolved in 200 ml dry dichloromethane and cooled to 0° C. To this mixture is dropped a solution of 32.5 g of benzotriazole (Fluka) and 31.4 ml of diisopropylamine (Fluka) in 150 ml of dichloromethane within 5 minutes. The mixture is stirred over night during which it reaches room temperature. The mixture is then extracted successively with water and brine. The organic phase is dried over sodium sulphate, filtered and evaporated to give an oil which is purified over a silica gel column (eluent: hexane/ethyl acetate: 4/1). 46.3 g of compound (23) are obtained as an oily substance.

$^1$H-NMR (CDCl$_3$, 300 MHz): 8.27 (d, 1H); 8.09 (d, 1H); 7.64 (t, 1H); 7.49 (t, 1H); 3.44 (t, 2H); 3.32 (t, 2H); 1.96 (quint., 2H); 1.65-1.76 (m, 2H); 1.55-1.64 (m, 2H).

6.7: Intermediate Compound 24

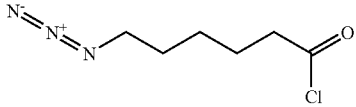

(24)

43.0 g of acid (25) are dissolved in 72 ml of toluene at 0° C. To this solution are added 68 ml of oxalyl chloride (Fluka) within 30 minutes whereby the temperature is kept below 5° C. The mixture is then stirred over night whereby it reaches room temperature. Evaporation of the solvent leaves 69.3 g of the crude acid chloride (24) which is used without further purifications.

$^1$H-NMR (CDCl$_3$, 300 MHz): 3.28 (t, 2H); 2.90 (t, 2H); 1.74 (quint., 2H); 1.61 (quint., 2H); 1.38-1.50 (m, 2H).

6.8: Intermediate Compound 25

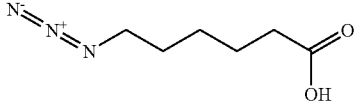

(25)

50.0 g of commercial 6-bromohexanoic acid are dissolved in 1.6 l of acetonitrile and treated with 166 g of sodium azide. The slurry is heated to 90° C. for about 16 hours until the starting material is consumed. The mixture is then cooled and filtered over celite. During evaporation of the solvent a further crop of salt precipitates and is subsequently removed via filtration. Finally the residue is taken up in ethyl acetate and filtered again. Evaporation of the solvent gives about 40 g of the azide (25).

$^1$H-NMR (CDCl$_3$, 300 MHz): 3.26 (t, 2H); 2.36 (t, 2H); 1.40-1.80 (m, 6H). IR: strong band at 2100 cm$^{-1}$.

Example 7

7.1: Protection of Pyrogallol

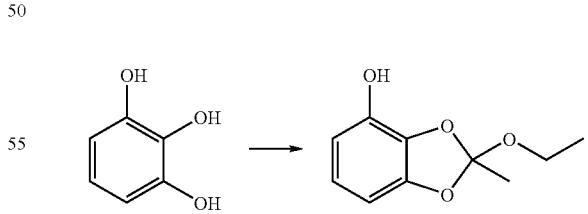

92.5 g of triethyl orthoacetate are added to 72.5 g of pyrogallol in 375 mL of xylene and heated at about 120° C.; the ethanol that forms is distilled off (theoretically about 66.5 mL), there then being formed a reddish-brown but clear solution. After cooling, the solution is washed with water (3×) and the organic phase is dried over sodium sulfate. After removal of the xylene, a residue remains, which is recrystallized from ethyl acetate/hexane. 67 g of product are obtained. Purification of the mother liquor on a column of silica gel (eluent hexane-ethyl acetate/1-1) yields a further 21.3 g of product (total yield: 88%).

7.2: Glucosylation of the Protected Pyrogallol

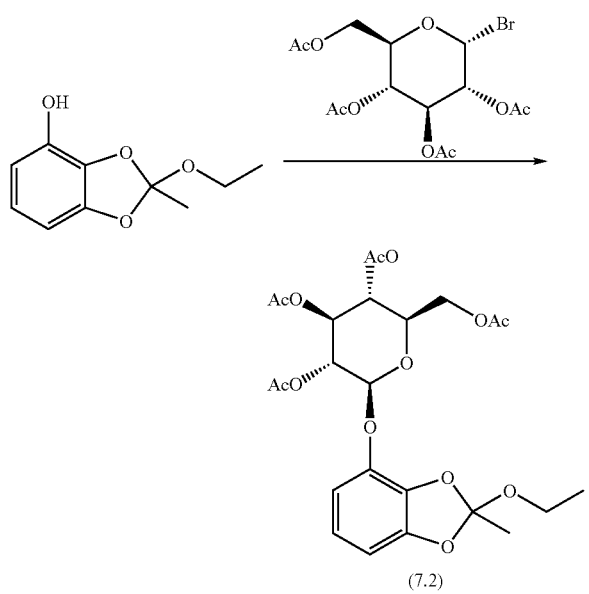

(7.2)

5.0 g of peracetylated α-D-glucosyl bromide (which is itself prepared from glucose penta-acetate and 48% HBr solution) and 1.2 g of protected pyrogallol are dissolved at RT in 15 mL of chloroform, and 4.2 g of potassium carbonate and 0.38 g of benzyltributylammonium chloride are added. The mixture is stirred over the weekend (but is presumably ready sooner!). The solid is filtered off and the organic phase is concentrated by evaporation. The residue is purified on silica gel (eluent hexane-ethyl acetate/10-3). 2.93 g (92%) of solid glucoside (7.2) are obtained (can be recrystallized if desired).

7.3: Deprotection of the Pyrogallol Moiety

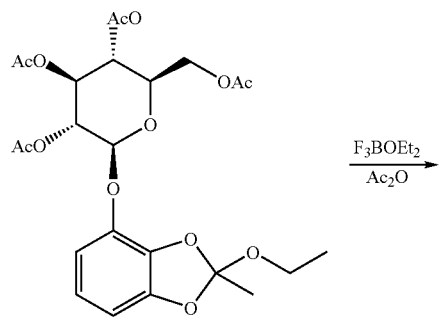

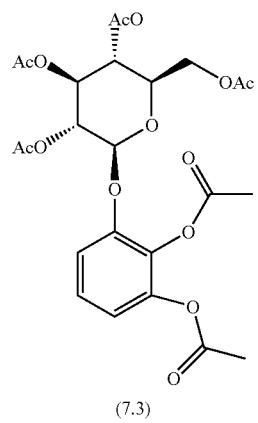

(7.3)

Under argon, 22.0 g of the sugar adduct 1086 are dissolved in a mixture of 110 mL of acetone and 110 mL of dry methylene chloride, adding 18.7 g of sodium iodide (to produce a clear solution) and then 6.9 mL of boron trifluoride etherate at from 0° to −5° C. The acetal is cleaved within a few minutes (5 min). The mixture is then poured into ice/water and extracted with methylene chloride. Drying with magnesium sulfate and removal of the solvent yield 19.0 g of a solid yellow foam. The foam is taken up in 200 mL of methylene chloride, and at 0° C. 18.9 mL of pyridine and 20.4 mL of acetic anhydride are added and stirring is carried out overnight at room temperature. The organic phase is extracted in succession with 1N hydrochloric acid (2×), saturated sodium hydrogen carbonate solution and brine. Drying is carried out over magnesium sulfate and the solvent is removed. The residue is recrystallized from methanol. 12.3 g of peracetylated compound (7.3) are obtained.

7.4: Deprotection of the Complete Molecule

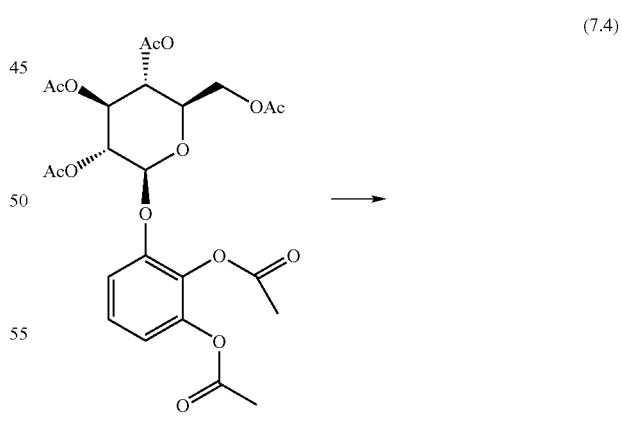

(7.4)

-continued

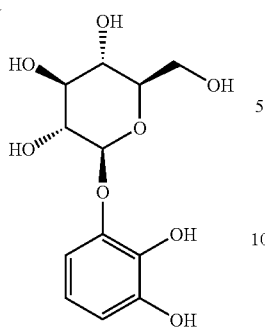

At room temperature, under argon, 26.8 g of the peracetylated compound (7.3) are introduced into 200 mL of dry methanol, and 48 mL of a 2M sodium methanolate solution are added. The solution immediately becomes clear, but darker in colour. After about 15 min, all the starting material has reacted. Neutralisation is carried out with weakly acidic ion exchanger Amberlite IRC (Fluka), the ion exchanger is filtered off and the filtrate is concentrated and lyophilised from water. The fully deprotected compound (7.4) is obtained in the form of a light-brown solid (12.0 g).

7.5: Enzymatic Reaction to Form the Benzofuranone Derivative A-27

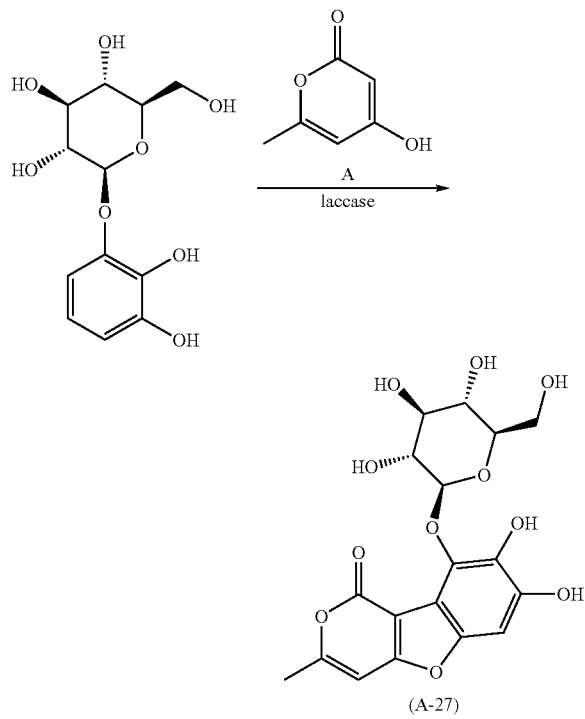

0.40 g of the compound (7.4) are dissolved together with 0.175 g of 4-hydroxy-methyl-pyranone (Fluka) in 40 mL of phosphate buffer (0.2M, pH=5) at room temperature, and 20.0 mg of laccase (*Trametes versicolor* (Fluka)) are added. For better solubility, 1 mL of ethanol is also added. The mixture is stirred in an open vessel until the starting materials can no longer be detected (about 2 days). The mixture is concentrated and the residue is taken up in methanol and centrifuged. The desired product (211 mg) is obtained in the form of a brownish-beige solid. The product can be purified further by reprecipitation from ether/methanol mixtures.

The DPPH Assay

For tests of antioxidative activity, the DPPH assay is used. DPPH (2,2-Diphenyl-1-picrylhydrazyl) is a stable radical, which absorbs in its radical form at 515 nm. Upon reduction by an antioxidant (AH), the absorption disappears:

$$DPPH• + AH \longrightarrow DPPH-H + A• \quad (1)$$

FIG. 1: The DPPH radical

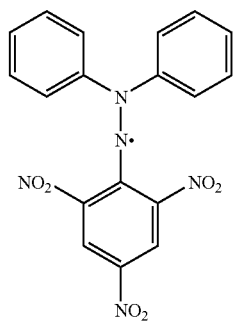

The rate of reaction (1) can be rather different for different antioxidants. In the case of the vitamins C and E, the equilibrium is reached in several minutes, however for other antioxidants it may also take hours. In the test, the ratio of the molar concentrations of the antioxidant and DPPH is varied (this ratio is named "EC"=efficient concentration), and the concentration of DPPH in the equilibrium state is measured for each ratio. Antiradical activity is defined as the amount of antioxidant necessary to decrease the initial DPPH-concentration by 50%, and is characterized by the so-called $EC_{50}$ value. The smaller the $EC_{50}$ value, the more efficient is the antioxidant. Thus, the inverse, $1/EC_{50}$, can be used to quantify the antiradical power.

In the following DPPH Assays the antioxidants listed in the Table below are used:

| Comp. No. | Structure/Antioxidant |
|---|---|
| (A-2) | 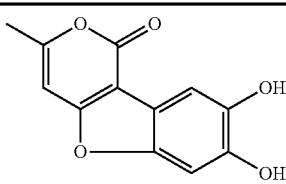 |
| (A-1) | 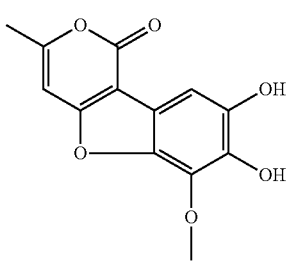 |

-continued

| Comp. No. | Structure/Antioxidant |
|---|---|
| (A-23) | [structure with H₃N⁺ Cl⁻ group, pyranone fused with benzofuran bearing two OH groups] |
| (101) (comparison) | Vitamin C |
| (102) (comparison) | Vitamin E |

Solutions of DPPH and the antioxidants in ethanol are prepared separately and added together for starting the reaction (0.5 cm³ of a 250 μM antioxidant solution is added to 2.5 cm³ of a 100 μM DPPH solution). The absorption is measured using a Perkin Elmer Lambda 20 spectrophotometer.

The investigated $EC_{50}$ values and the inverse, $1/EC_{50}$ values, are listed in the table below:

| Comp. No. | $EC_{50}$ values | $1/EC_{50}$ values |
|---|---|---|
| (A-2) | 0.1965 | 5.09 |
| (A-1) | 0.1201 | 8.33 |
| (A-23) | 0.0750 | 13.33 |
| (101) | 0.243 | 4.11 |
| (102) | 0.247 | 4.05 |

The compounds Nos. A-1, A-2 and A-23 according to the present invention possess significantly higher antioxidant/radical power measured in $EC_{50}$ values and the $1/EC_{50}$ values compared to the state-of-the-art antioxidants of formula (101) and (102). Similar results are obtained with compounds A-3 to A-18, A-20 to A-24, A-27 to A-28, B-1 to B-4.

Example 6

Composition According to the Invention in the Form of a Lotion (Water/Oil Emulsion)

| | % |
|---|---|
| Cyclomethicone | 25.00 |
| Polyglyceryl-2-sesquiisostearate/Beeswax/Mineral Oil/Magnesium Stearate/Aluminium Stearate, such as commercialized under "Hostacerin WO" by HOECHST | 12.00 |
| Phenyl Dimethicone | 6.00 |
| Dimethicone | 3.00 |
| Isopropyl Myristate | 3.50 |
| BHT | 0.05 |
| Water | q.s.p. |
| C12-15 Alkyl Benzoate | 3.00 |
| Methyl 4-hydroxybenzoate | 0.16 |
| Propyl 4-hydroxybenzoate | 0.05 |
| 2-phenoxyethanol | 0.58 |
| β-sitosterol | 0.50 |
| Disodium EDTA | 0.10 |
| Compound according to this invention (A-1) | 0.05 |
| Total | 100.00% |

Equivalent formulations are obtained using the same amount of compound A-2, A-3, A-4, A-5, A-6, A-7, A-8, A-9, A-10, A-11, A-12, A-13, A-14, A-15, A-16, A-17, A-18, A-20, A-21, A-22, A-23, A-24, A-26, A-27, A-28, B-1, B-2, B-3, or B-4 instead of compound No. A-1. While there have been shown, described and pointed out the features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention.

The invention claimed is:

1. A stabilized composition which comprises (a) an organic material selected from the group consisting of natural or synthetic organic polymers, cosmetical formulations, pharmaceutical formulations and food products which material is subject to degradation by exposure to UV radiation and/or deleterious effects of radicals and (b) an effective stabilizing amount of a compound of general formula (I)

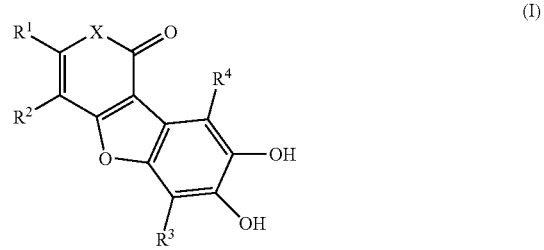

wherein
X is O, NH or $NR^{15}$;
$R^1$, $R^2$, $R^3$ and $R^4$ are independently of each other H, halogen, hydroxy, $C_1$-$C_{24}$alkyl which is substituted by at least one E and/or interrupted by at least one D, $C_1$-$C_{24}$perfluoroalkyl, $C_6$-$C_{14}$perfluoroaryl, $C_5$-$C_{12}$cycloalkyl; $C_5$-$C_{12}$cycloalkyl which is substituted by G and/or interrupted by —S—, —O—, or —$NR^{15}$—; —$NR^{15}R^{16}$; $C_1$-$C_{24}$alkylthio; —$PR^{17}R^{18}$; $C_5$-$C_{12}$cycloalkoxy; $C_5$-$C_{12}$cycloalkoxy which is substituted by G; $C_6$-$C_{24}$aryl; $C_6$-$C_{24}$aryl which is substituted by G, $C_5$-$C_{12}$cycloalkyl, $C_7$-$C_{25}$aralkyl, $C_6$-$C_{14}$perfluoroaryl, or $C_1$-$C_{24}$haloalkyl; $C_2$-$C_{20}$heteroaryl; $C_2$-$C_{20}$heteroaryl which is substituted by G, $C_1$-$C_{24}$alkyl, $C_5$-$C_{12}$cycloalkyl, $C_7$-$C_{25}$aralkyl, $C_6$-$C_{14}$perfluoroaryl, or $C_1$-$C_{24}$haloalkyl; $C_2$-$C_{24}$alkenyl; $C_2$-$C_{24}$alkynyl; $C_1$-$C_{24}$alkoxy; $C_1$-$C_{24}$alkoxy which is substituted by at least one E and/or interrupted by at least one D; $C_7$-$C_{25}$aralkyl; $C_7$-$C_{25}$aralkyl, which is substituted by G; $C_7$-$C_{25}$aralkoxy, $C_7$-$C_{25}$aralkoxy which is substituted by G; or —OCO—$R^{19}$ or —CO—$R^{19}$, or
$R^1$ and $R^2$ together are a group

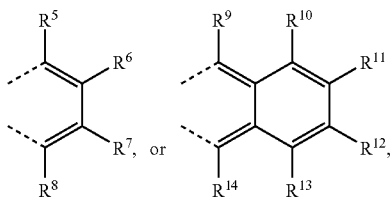

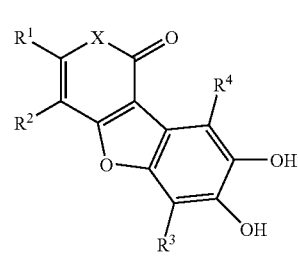

(I)

wherein $R^5$, $R^6$, $R^7$, $R^8$, $R^9$, $R^{10}$, $R^{11}$, $R^{12}$, $R^{13}$ and $R^{14}$ are independently of each other H, halogen, hydroxy, $C_1$-$C_{24}$alkyl, $C_1$-$C_{24}$alkyl which is substituted by at least one E and/or interrupted by at least one D, $C_1$-$C_{24}$ perfluoroalkyl, $C_6$-$C_{14}$perfluoroaryl, $C_5$-$C_{12}$cycloalkyl, $C_5$-$C_{12}$cycloalkyl which is substituted by at least one G and/or interrupted by at least one S—, —O—, or —$NR^{15}$—, $C_5$-$C_{12}$cycloalkoxy, $C_5$-$C_{12}$cycloalkoxy which is substituted by G, $C_6$-$C_{24}$aryl, $C_5$-$C_{24}$aryl which is substituted by at least one G, $C_2$-$C_{20}$heteroaryl, $C_2$-$C_{20}$heteroaryl which is substituted by at least one G, $C_2$-$C_{24}$alkenyl, $C_2$-$C_{24}$alkynyl, $C_1$-$C_{24}$alkoxy, $C_1$-$C_{24}$alkoxy which is substituted by at least one E and/or interrupted by at least one D, $C_7$-$C_{25}$aralkyl, $C_7$-$C_{25}$aralkyl, which is substituted by at least one G, $C_7$-$C_{25}$aralkoxy, $C_7$-$C_{25}$aralkoxy which is substituted by at least one G, or are —CO—$R^{19}$, D is —CO—; —COO—; —S—; —SO—; —$SO_2$—; —O—; —$NR^{15}$—; —$POR^{17}$—; —$CR^{20}$=$CR^{21}$—; or —C≡C—;

E is —$OR^{22}$; —$SR^{22}$; —$NR^{15}R^{16}$; —[$NR^{15}R^{16}R^{24}$]$^+Z^-$; —$COR^{19}$; —$COOR^{23}$; —$CONR^{15}R^{16}$; —CN; —$N_3$; —$OCOOR^{23}$; or halogen; and G is E, or $C_1$-$C_{24}$alkyl, wherein $R^{20}$, $R^{21}$, $R^{15}$, $R^{16}$ and $R^{24}$ are independently of each other H; $C_6$-$C_{18}$aryl; $C_6$-$C_{18}$aryl which is substituted by $C_1$-$C_{24}$alkyl and/or $C_1$-$C_{24}$alkoxy; $C_1$-$C_{24}$alkyl; or $C_1$-$C_{24}$alkyl which is interrupted by at least one —O—; or $R^{15}$ and $R^{16}$ together form a five or six membered ring, Z is an equivalent of an anion;

$R^{19}$ is H; $C_6$-$C_{18}$aryl; $C_6$-$C_{18}$aryl which is substituted by $C_1$-$C_{24}$alkyl, hydroxy and/or $C_1$-$C_{24}$alkoxy; $C_6$-$C_{18}$aryloxy; $C_6$-$C_{18}$aryloxy which is substituted by $C_1$-$C_{24}$alkyl, hydroxy and/or $C_1$-$C_{24}$alkoxy; $C_1$-$C_{24}$alkyl; or $C_1$-$C_{24}$alkyl which is interrupted by at least one —O—; $C_1$-$C_{24}$alkoxy; or $C_1$-$C_{24}$alkoxy which is interrupted by at least one —O—;

$R^{22}$ and $R^{23}$ are independently of each other H; $C_6$-$C_{15}$aryl; $C_6$-$C_{18}$aryl, which is substituted by $C_1$-$C_{24}$alkyl or $C_1$-$C_{24}$alkoxy; $C_1$-$C_{24}$alkyl; or $C_1$-$C_{24}$alkyl which is interrupted by at least one —O—; and $R^{17}$ and $R^{18}$ are independently of each other $C_1$-$C_{24}$alkyl, $C_6$-$C_{15}$aryl, or $C_6$-$C_{18}$aryl, which is substituted by $C_1$-$C_{24}$alkyl;

$R^3$ and/or $R^4$ may further be a mono-, di- or oligosaccharide residue alpha- or beta-linked to the phenolic ring system either directly or via the phenolic oxygen.

2. The stabilized composition according to claim 1 which comprises (a) an organic material subject to degradation by exposure to UV radiation and/or deleterious effects of radicals and (b) an effective stabilizing amount of a compound of general formula (I)

wherein

X is O, NH or $NR^{15}$;

$R^1$, $R^2$, $R^3$ and $R^4$ are independently of each other H, halogen, hydroxy, $C_1$-$C_{24}$alkyl which is substituted by at least one E and/or interrupted by at least one D, $C_1$-$C_{24}$ perfluoroalkyl, $C_6$-$C_{14}$perfluoroaryl, $C_5$-$C_{12}$cycloalkyl, $C_5$-$C_{12}$cycloalkyl which is substituted by G and/or interrupted by S—, —O—, or —$NR^{15}R^{16}$, $C_1$-$C_{24}$alkylthio, —$PR^{17}R^{16}$, $C_5$-$C_{12}$cycloalkoxy, $C_5$-$C_{12}$cycloalkoxy which is substituted by G, $C_6$-$C_{24}$aryl, $C_6$-$C_{24}$aryl which is substituted by G, $C_5$-$C_{12}$cycloalkyl, $C_7$-$C_{25}$aralkyl, $C_1$-$C_{24}$ perfluoroalkyl, $C_6$-$C_{14}$perfluoroaryl, or $C_1$-$C_{24}$haloalkyl; $C_2$-$C_{20}$heteroaryl, $C_2$-$C_{20}$heteroaryl which is substituted by G, fluorine, $C_1$-$C_{24}$alkyl, $C_5$-$C_{12}$cycloalkyl, $C_7$-$C_{25}$aralkyl, $C_1$-$C_{24}$ perfluoroalkyl, $C_6$-$C_{14}$ perfluoroaryl, or $C_1$-$C_{24}$haloalkyl; $C_2$-$C_{24}$alkenyl, $C_2$-$C_{24}$alkynyl, $C_1$-$C_{24}$alkoxy, $C_1$-$C_{24}$alkoxy which is substituted by at least one E and/or interrupted by at least one D, $C_7$-$C_{25}$aralkyl, $C_7$-$C_{25}$aralkyl, which is substituted by G, $C_7$-$C_{25}$aralkoxy, $C_7$-$C_{25}$aralkoxy which is substituted by G, or —CO—$R^{19}$, or $R^1$ and $R^2$ are a group

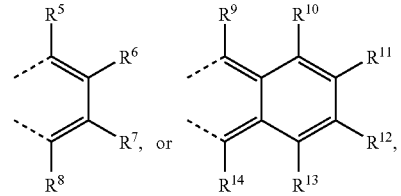

wherein $R^5$, $R^6$, $R^7$, $R^8$, $R^9$, $R^{10}$, $R^{11}$, $R^{12}$, $R^{13}$ and $R^{14}$ are independently of each other H, halogen, hydroxy, $C_1$-$C_{24}$alkyl, $C_1$-$C_{24}$alkyl which is substituted by at least one E and/or interrupted by at least one D, $C_1$-$C_{24}$ perfluoroalkyl, $C_6$-$C_{14}$ perfluoroaryl, $C_5$-$C_{12}$cycloalkyl, $C_5$-$C_{12}$cycloalkyl which is substituted by at least one G and/or interrupted by at least one S—, —O—, or —$NR^{15}$—, $C_5$-$C_{12}$cycloalkoxy, $C_5$-$C_{12}$cycloalkoxy which is substituted by G, $C_6$-$C_{24}$aryl, $C_6$-$C_{24}$aryl which is substituted by at least one G, $C_2$-$C_{20}$heteroaryl, $C_2$-$C_{20}$heteroaryl which is substituted by at least one G, $C_2$-$C_{24}$alkenyl, $C_2$-$C_{24}$alkynyl, $C_1$-$C_{24}$alkoxy, $C_1$-$C_{24}$alkoxy which is substituted by at least one E and/or interrupted by at least one D, $C_7$-$C_{25}$aralkyl, $C_7$-$C_{25}$aralkyl, which is substituted by at least one G, $C_7$-$C_{25}$aralkoxy, $C_7$-$C_{25}$aralkoxy which is substituted by at least one G, or at least —CO—$R^{19}$, D is —CO—; —COO—; —S—; —SO—; —$SO_2$—; —O—; —$NR^{25}$—; —$POR^{17}$—; —$CR^{20}$=$CR^{21}$—; or —C≡C—;

E is —OR²²; —SR²²; —NR¹⁵R¹⁶; —[NR¹⁵R¹⁶R²⁴]⁺Z⁻; —COR¹⁶; —COOR²³; —CONR¹⁵R¹⁶; —CN; —N₃; —OCOOR²³; or halogen; and G is E, or $C_1$-$C_{24}$alkyl, wherein $R^{20}$, $R^{21}$, $R^{15}$, $R^{16}$ and $R^{24}$ are independently of each other H; $C_6$-$C_{18}$aryl; $C_6$-$C_{18}$aryl which is substituted by $C_1$-$C_{24}$alkyl, or $C_1$-$C_{24}$alkoxy; $C_1$-$C_{24}$alkyl; or $C_1$-$C_{24}$alkyl which is interrupted by at least one —O—; or $R^{15}$ and $R^{16}$ together form a five or six membered ring which is

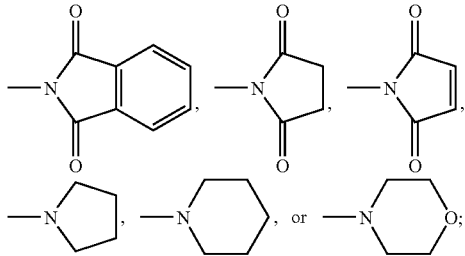

Z is halogen;

$R^{19}$ and $R^{23}$ are independently of each other H; $C_6$-$C_{18}$aryl; $C_6$-$C_{18}$aryl which is substituted by $C_1$-$C_{24}$alkyl, or $C_1$-$C_{24}$alkoxy; $C_1$-$C_{24}$alkyl; or $C_1$-$C_{24}$alkyl which is interrupted by at least one —O—;

$R^{22}$ is H; $C_5$-$C_{18}$aryl; $C_6$-$C_{18}$aryl, which is substituted by $C_1$-$C_{24}$alkyl, or $C_1$-$C_{24}$alkoxy; $C_1$-$C_{24}$alkyl; or $C_1$-$C_{24}$alkyl which is interrupted by at least one —O—; and $R^{17}$ and $R^{18}$ are independently of each other $C_1$-$C_{24}$alkyl, $C_6$-$C_{18}$aryl, or $C_6$-$C_{18}$aryl, which is substituted by $C_1$-$C_{24}$alkyl;

$R^3$ and/or $R^4$ may further be a mono-, di- or oligosaccharide residue alpha- or beta-linked to the phenolic ring system either directly or via the phenolic oxygen.

3. The composition according to claim 1 containing component (b) in an amount of 0.001 to 20% by weight, based on the total weight of the composition.

4. The composition according to claim 1 which additionally contains an effective stabilizing amount of a further component selected from the group consisting of benzophenones, benzotriazoles, cyanoacrylic acid derivatives, hydroxyaryl-s-triazines, anthranilates, dibenzoyl methanes, benzylidene-dioxoimidazolines, benzylidene malonates, inorganic oxides, salicylates, cinnamate derivatives, para-aminobenzoic acid derivatives, camphor derivatives, phenylbenzimidazoles, diphenylacrylates, organic nickel compounds, oxanilides; antioxidants, p-hydroxybenzoic acid or its derivatives, coumarin derivatives, flavones, hydroxyphenyl propanoic acid derivatives, uric or tannic acid or its derivatives, hydroquinone, and sterically hindered amines.

5. The composition according to claim 2, wherein the compound of formula (I)

X is O, NH or $NR^{15}$;

$R^1$ is $C_1$-$C_{24}$alkyl, $C_2$-$C_{24}$alkenyl, $C_1$-$C_{24}$alkoxy, or said alkyl, alkenyl or alkoxy which is substituted by E;

$R^2$ is H;

$R^3$ is H; hydroxy; $C_1$-$C_{24}$alkyl; $C_1$-$C_{24}$alkyl which is substituted by at least one E and/or interrupted by at least one D; $C_5$-$C_{12}$cycloalkyl; $C_5$-$C_{12}$cycloalkyl which is substituted by G and/or interrupted by —O— or —NR¹⁵—; —NR¹⁵R¹⁶; $C_5$-$C_{12}$cycloalkoxy; $C_5$-$C_{12}$cycloalkoxy which is substituted by G; phenyl which is unsubstituted or substituted by G; $C_2$-$C_{24}$alkenyl; $C_1$-$C_{24}$alkoxy; $C_1$-$C_{24}$alkoxy which is substituted by at least one E and/or interrupted by at least one D; $C_7$-$C_{25}$phenylalkyl; $C_7$-$C_{25}$phenylalkyl, which is substituted by G; $C_7$-$C_{25}$phenylalkoxy; $C_7$-$C_{25}$phenylalkoxy which is substituted by G; or —OCO—R¹⁹ or —CO—R¹⁹;

$R^4$ is H; hydroxy; $C_1$-$C_{24}$alkyl which is unsubstituted or substituted by at least one E, and/or is interrupted by at least one D; $C_5$-$C_{12}$cycloalkoxy; $C_5$-$C_{12}$cycloalkoxy which is substituted by G; $C_1$-$C_{24}$alkoxy; $C_1$-$C_{24}$alkoxy which is substituted by at least one E and/or interrupted by at least one D; or —OCO—R¹⁹ or —CO—R¹⁹;

$R^3$ and/or $R^4$ may further be a mono-, di- or oligosaccharide residue alpha- or beta-linked to the phenolic ring system wherein said residue consists of hexose or pentose subunits and wherein at least one hexose or pentose subunit is selected from the group consisting of glucose, ribose, galactose, mannose, N-acetyl glucosamine, N-acetyl galactosamine, lactose and N-acetyl lactosamine;

D is —CO—, —COO—, or —O—;

G and E are independently of each other —OR²²; —NR¹⁵R¹⁶; —[NR¹⁵R¹⁶R²⁴]⁺Z⁻; —COR¹⁹; —COOR²³; —CN; —N₃; —OCOOR²³; or halogen; or G is $C_1$-$C_{12}$alkyl;

$R^{15}$ and $R^{16}$ and $R^{24}$ are independently of each other H; phenyl; phenyl which is substituted by $C_1$-$C_{24}$alkyl; or $C_1$-$C_{24}$alkoxy; $C_1$-$C_{24}$alkyl; or $C_1$-$C_{24}$alkyl which is interrupted by —O—;

$R^{19}$ is H; phenyl; phenyl which is substituted by $C_1$-$C_{24}$alkyl, hydroxy and/or $C_1$-$C_{24}$alkoxy; $C_1$-$C_{24}$alkyl;

or $C_1$-$C_{24}$alkyl which is interrupted by —O—; phenoxy; phenoxy which is substituted by $C_1$-$C_{24}$alkyl, hydroxy and/or $C_1$-$C_{24}$alkoxy; $C_1$-$C_{24}$alkoxy; or $C_1$-$C_{24}$alkoxy which is interrupted by —O—;

$R^{22}$ and $R^{23}$ are independently of each other H; phenyl; phenyl which is substituted by $C_1$-$C_{24}$alkyl; $C_1$-$C_{24}$alkyl; or $C_1$-$C_{24}$alkyl which is interrupted by —O—.

6. The composition according to claim 1, wherein the compound of formula (I)

X is O, NH or $NR^{15}$;

$R^1$ is $C_1$-$C_{24}$alkyl, $C_2$-$C_{24}$alkenyl, or said alkyl or alkenyl substituted by —NR¹⁵R¹⁶ or —N₃ or —[NR¹⁵R¹⁶R²⁴]⁺Z⁻;

$R^2$ is H;

$R^3$ and $R^4$ independently are H; hydroxy; $C_1$-$C_{12}$alkyl; $C_2$-$C_{12}$alkenyl; $C_1$-$C_{12}$alkoxy; or —OCO—R¹⁹ or —CO—R¹⁹; or are a mono- or di-saccharide residue alpha- or beta-linked to the phenolic ring system wherein said residue consists of hexose or pentose subunits selected from the group consisting of glucose, ribose, galactose, mannose, N-acetyl glucosamine, N-acetyl galactosamine, lactose and N-acetyl lactosamine;

$R^{15}$, $R^{16}$ and $R^{24}$ are independently of each other H or $C_1$-$C_5$alkyl, and $Z^-$ is halogenide.

7. The composition according to claim 1 wherein the compound of component (b) is selected from the group consisting of:

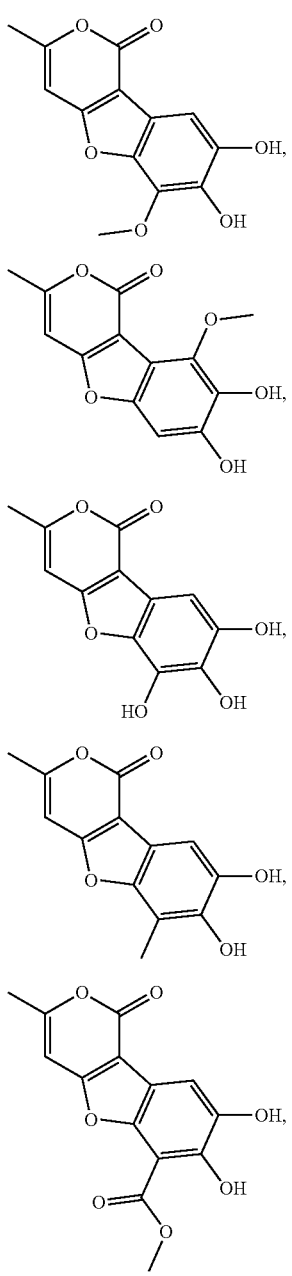
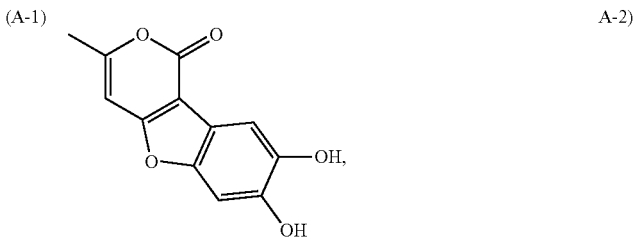
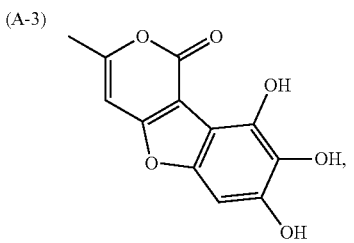
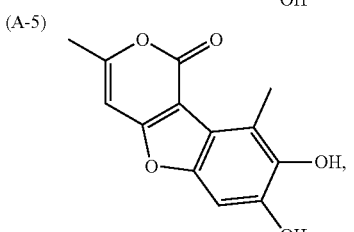
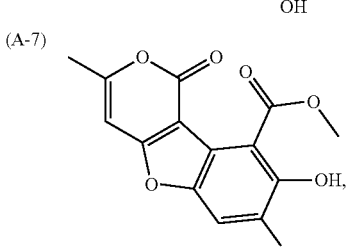
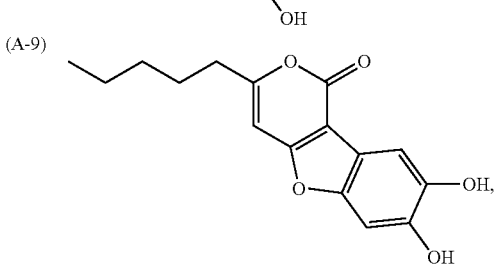
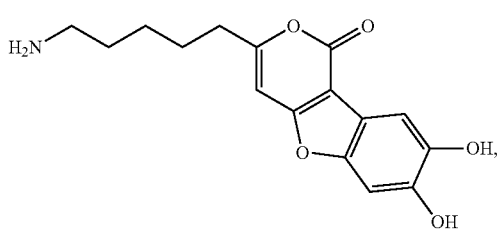
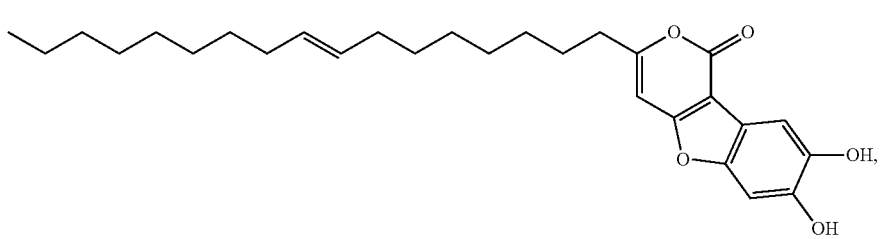

8. The composition according to claim 1 which is a cosmetic composition intended for make-up comprising a compound of general formula (I) wherein said cosmetic composition is in the form of foundation, pressed powder, face powder, lipstick, eye shadow, eyebrow pencil, eye liner, mascara, anhydrous or hydrated emulsion or paste and wherein said cosmetic composition additionally comprises cosmetically acceptable ingredients which include oils, waxes, surfactants, silicones, perfluorides, synthetic organic UV-absorbers and fragrances.

9. The composition according to claim 1 which is a dermatological, pharmaceutical or food product comprising a compound of general formula (I).

10. A method of enhancing the photo stability of cosmetical or dermatological compositions by incorporation therein an effective stabilizing amount of a compound of general formula (I) according to claim 1.

11. The method according to claim 10, further including a cosmetically or pharmaceutically acceptable carrier and a further organic UV absorber.

12. The method according to claim 10, wherein the cosmetical or dermatological compositions further contain oxidation-sensitive and/or UV-sensitive active ingredients.

13. The method according to claim 12, wherein the cosmetical or dermatological compositions are sunscreen formulations for UV-protection of human or animal skin and/or hair.

14. The method according to claim 10, wherein the cosmetical or dermatological compositions further comprise a UV absorber selected from the group consisting of cinnamic acid derivatives and di-benzoyl methane derivatives.

* * * * *